US009856296B2

(12) United States Patent
Takkinen et al.

(10) Patent No.: US 9,856,296 B2
(45) Date of Patent: Jan. 2, 2018

(54) HYPOALLERGEN

(75) Inventors: Kristiina Takkinen, Espoo (FI); Marja-Leena Laukkanen, Espoo (FI); Hans Söderlund, Espoo (FI); Sirpa Jylhä, Espoo (FI); Heidi Holkeri, Espoo (FI); Merja Niemi, Joensuu (FI); Janne Jänis, Joensuu (FI); Juha Rouvinen, Joensuu (FI)

(73) Assignee: DESENTUM OY, Helsinki (FI)

( * ) Notice: Subject to any disclaimer, the term of this patent is extended or adjusted under 35 U.S.C. 154(b) by 0 days.

(21) Appl. No.: 14/112,207

(22) PCT Filed: Apr. 18, 2012

(86) PCT No.: PCT/EP2012/057046
§ 371 (c)(1),
(2), (4) Date: Oct. 16, 2013

(87) PCT Pub. No.: WO2012/143374
PCT Pub. Date: Oct. 26, 2012

(65) Prior Publication Data

US 2014/0037663 A1 Feb. 6, 2014

Related U.S. Application Data

(60) Provisional application No. 61/476,488, filed on Apr. 18, 2011.

(30) Foreign Application Priority Data

Apr. 18, 2011 (FI) ..................................... 20115374

(51) Int. Cl.

| | |
|---|---|
| ***A61K 39/00*** | (2006.01) |
| ***A61K 39/35*** | (2006.01) |
| ***A61K 39/36*** | (2006.01) |
| ***C07K 1/00*** | (2006.01) |
| ***C07K 14/00*** | (2006.01) |
| ***C07K 17/00*** | (2006.01) |
| ***C07K 14/415*** | (2006.01) |

(52) U.S. Cl.
CPC ............ *C07K 14/415* (2013.01); *A61K 39/36* (2013.01)

(58) Field of Classification Search
None
See application file for complete search history.

(56) References Cited

U.S. PATENT DOCUMENTS

2004/0043438 A1* 3/2004 Holm et al. ................ 435/7.92

FOREIGN PATENT DOCUMENTS

| | | | | |
|---|---|---|---|---|
| JP | 2004/521618 A | | 7/2004 | |
| WO | WO 92/02621 | * | 2/1992 | ............ C12N 15/29 |
| WO | WO 02/40676 A2 | | 5/2002 | |
| WO | WO 03/096869 A2 | | 11/2003 | |
| WO | WO 2004/047794 A2 | | 6/2004 | |
| WO | WO 2006/050729 A2 | | 5/2006 | |
| WO | WO 2007/073907 A1 | | 7/2007 | |
| WO | WO 2008/092992 A1 | | 8/2008 | |
| WO | WO 2008/098277 A2 | | 8/2008 | |
| WO | WO 2009/024208 A1 | | 2/2009 | |
| WO | WO 2010/018378 A2 | | 2/2010 | |
| WO | WO 2010/089671 A2 | | 8/2010 | |

OTHER PUBLICATIONS

Hoffman-Sommergruber et al. 'Genomic characterization of members of the Bet v 1 family: genes coding for allergens and pathogenesis-related proteins share intron positions.' Gene 197:91-100, 1997.*
Breiteneder et al., Four recombinant isoforms of Cor a I, the major allergen of hazel pollen, show different IgE-binding properties, Eur. J. Biochem. vol. 212, pp. 355-362, 1993.*
GenBank Accession No. AAC13315. Apr. 13, 1998.*
Karamloo et al. 'Pyr c 1, the major allergen from pear (*Pyrus communis*), is a new member of the Bet v 1 allergen family.' J. Chromatogr B Biomed Sci Appl. 756(1-2):281-293, 2001.*
Kuby et al. 'Immunology.' Fourth Edition, Chapter 18: 449-465, 2001.*
Kuby Immunology, 4th Edition, Chapter 18, "Vaccines," pp. 449-465 (2001).*
Hoffman et al. 'Novel approaches and perspectives in allergen immunotherapy.' Allergy 2017; DOI: 10.1111/all.13135. pp. 1-13.*
Garman et al., "Structure of the Fc fragment of human IgE bound to its high-affinity receptor Fcε RIα" *Nature* (Jul. 20, 2000), vol. 406, pp. 259-266.
Gronlund, H. and G. Gafvelin, "Recombinant Bet v 1 vaccine for treatment of allergy to birch pollen," *Human Vaccines* (Dec. 2010), vol. 6, No. 12, pp. 970-977.
Holm et al., "Allergy Vaccine Engineering: Epitope Modulation of Recombinant Bet v 1 Reduces IgE Binding but Retains Protein Folding Pattern for Induction of Protective Blocking-Antibody Responses," *The Journal of Immunology* (2004), vol. 173, pp. 5258-5267.
IUPAC-IUB Joint Commission on Biochemical Nomenclature (JCBN), Nomenclature and Symbolism for Amino Acids and Peptides, Recommendations 1983, *Eur. J. Biochem.* (1984), vol. 138, pp. 9-37.

(Continued)

*Primary Examiner* — Nora Rooney
(74) *Attorney, Agent, or Firm* — Birch, Stewart, Kolasch & Birch, LLP

(57) ABSTRACT

The present invention provides mutant polypeptides useful as hypoallergens. More specifically the present invention provides mutant Bet v 1 proteins and the use of such polypeptides as hypoallergens for desensitizing against birch pollen allergies. Furthermore, the invention provides vaccine formulations comprising such polypeptides; the use of such formulations; and to methods of vaccination against birch pollen allergy.

10 Claims, 7 Drawing Sheets
(4 of 7 Drawing Sheet(s) Filed in Color)

(56) References Cited

OTHER PUBLICATIONS

Jenkins et al., "Structural relatedness of plant food allergens with specific reference to cross-reactive allergens: An in silico analysis," *J. Allergy Clin. Immunol.* (2005), vol. 115, pp. 163-170.
Knoll, E. F., "Requirements for effective IgE cross-linking on mast cells and basophils," *Mol. Nutr. Food Res.* (2006), vol. 50, pp. 620-624.
Laver et al., "Epitopes on Protein Antigens: Misconceptions and Realities," *Cell* (May 18, 1990), vol. 61, pp. 553-556.
Niederberger et al., "Vaccination with genetically engineered allergens prevents progression of allergic disease," *PNAS* (Oct. 5, 2004), vol. 101, Suppl. 2, pp. 14677-14682.
Niemi et al., "Molecular Interactions Between a Recombinant IgE Antibody and the β-Lactoglobulin Allergan," *Structure* (Nov. 2007), vol. 15, pp. 1413-1421.
Radauer et al., "Allergens are distributed into few protein families and possess a restricted number of biochemical functions," *J. Allergy Clin. Immunol.* (2008), vol. 121, pp. 847-852.
Rouvinan et al., "Transient Dimers of Allergens," *PLoS ONE* (Feb. 2010), vol. 5, No. 2, E9037, pp. 1-9.
Search Report dated Dec. 28, 2011, in Finnish Patent Application No. 20115374.
Takkinen et al., "An active single-chain antibody containing a cellulase linker domain is secreted by *Escherichia coli," Protein Engineering* (1991), vol. 4, No. 7, pp. 837-841.
Valenta et al., "From Allergen Genes to Allergy Vaccines," *Annu. Rev. Immunol.* (2010), vol. 28, pp. 211-241.
Wagner et al., "Naturally occurring hypoallergenic Bet v 1 isoforms fail to induce IgE responses in individuals with birch pollen allergy," *J. Allergy Clin. Immunol.* (2008), vol. 121, pp. 246-252.
Wallner et al., "Reshaping the Bet v 1 fold moldulates $T_H$ polarization," *J. Allergy Clin. Immunol.* (2011), vol. 127, pp. 1571-1578.
Wan et al., "The crystal structure of IgE Fc reveals an asymetrically bent conformation," *Nature Immunology* (Jul. 2002), vol. 3, No. 7, pp. 681-686.
Notification of First Office Action dated Sep. 9, 2014, in Chinese Patent Application No. 201280026275.1, with English translation.
Japanese Office Action issued in Japanese Patent Application No. 2014-505596 dated Feb. 23, 2016.

* cited by examiner

Fig. 4

A (rBet v 1 wt)

GGCGTGTTTAACTATGAAACCGAAACCACCAGCGTGATTCCGGCGGCGCGTC
TGTTTAAAGCGTTTATTCTGGATGGCGATAACCTGTTTCCGAAAGTGGCGCCGCAGGCGA
TTAGCAGCGTGGAAAACATTGAAGGCAACGGCGGCCCGGGCACCATTAAGAAAATCAGCT
TCCCGGAAGGCTTTCCGTTCAAATACGTGAAAGATCGTGTGGATGAAGTGGATCATACCA
ACTTCAAATACAACTACAGCGTGATTGAAGGCGGCCCGATTGGCGATACCCTGGAAAAAA
TTAGCAACGAAATTAAAATTGTGGCGACCCCGGATGGCGGCAGCATTCTGAAAATTAGCA
ACAAATATCATACCAAAGGCGATCATGAAGTGAAAGCGGAACAGGTGAAAGCGAGCAAAG
AAATGGGCGAAACCCTGCTGCGTGCGGTGGAAAGCTATCTGCTGGCGCATAGCGATGCGT
ATAACTAA

B (Bet v 1 N28K + E101K)

GGCGTGTTTAACTATGAAACCGAAACCACCAGCGTGATTCCGGCGGCGCGTC
TGTTTAAAGCGTTTATTCTGGATGGCGATAAACTGTTTCCGAAAGTGGCGCCGCAGGCGA
TTAGCAGCGTGGAAAACATTGAAGGCAACGGCGGCCCGGGCACCATTAAGAAAATCAGCT
TCCCGGAAGGCTTTCCGTTCAAATACGTGAAAGATCGTGTGGATGAAGTGGATCATACCA
ACTTCAAATACAACTACAGCGTGATTGAAGGCGGCCCGATTGGCGATACCCTGGAAAAAA
TTAGCAACAAAATTAAAATTGTGGCGACCCCGGATGGCGGCAGCATTCTGAAAATTAGCA
ACAAATATCATACCAAAGGCGATCATGAAGTGAAAGCGGAACAGGTGAAAGCGAGCAAAG
AAATGGGCGAAACCCTGCTGCGTGCGGTGGAAAGCTATCTGCTGGCGCATAGCGATGCGT
ATAACTAA

HYPOALLERGEN

CROSS REFERENCE TO RELATED APPLICATIONS

This non-provisional application is a National Stage entry under U.S.C. §371 of International Application No. PCT/EP2012/057046 filed on Apr. 18, 2012, which claims the benefit of Finnish Patent Application No. 20115374 filed in Finland on Apr. 18, 2011 and to U.S. Provisional Application No. 61/476,488 filed on Apr. 18, 2011. The entire contents of all of the above applications are hereby incorporated by reference.

FIELD OF THE INVENTION

The present invention relates to mutant polypeptides useful as hypoallergens. More specifically the present invention relates to specific mutant Bet v 1 polypeptides and to the use of such polypeptides as hypoallergens for desensitizing against birch pollen allergies. Furthermore, the invention relates to vaccine formulations comprising such polypeptides; to the use of such formulations in vaccination; and to methods of vaccination against birch pollen allergy.

BACKGROUND OF THE INVENTION

Allergies are caused by the immune reaction to commonly harmless proteins, allergens. Allergic diseases are reaching epidemic proportions all over the world. More than 25% of the population in industrialized countries suffer from type I allergy and the number is steadily increasing. Birch pollen allergy is a very common form of type I allergy. Bet v 1 is the major allergen of birch pollen. More information on the Bet v 1 allergen, its isoallergens and variants, is found on the WHO website www.allergen.org.

Type I allergy is based on the formation of immunoglobulin E (IgE) antibodies. The symptoms occur when an allergen molecule binds to two IgE antibodies bound to receptors on a mast cell or basophile surface and induces cross-linking of the IgE-FcϵRI complexes. This triggers the degranulation of biological mediators, such as histamine and lipid mediators, which cause inflammatory reactions and symptoms, such as allergic asthma, rhinitis, food and skin allergy, and even anaphylaxis.

The IgE is a large molecule that consists of two identical light and heavy chains. There are five domains in the heavy chain of IgE: VH, Cϵ1, Cϵ2, Cϵ3 and Cϵ4. The size of the complete IgE molecule is about 200 kDa. The crystal structures of the Cϵ2-Cϵ4 fragment bound to its FcϵRI receptor and the Cϵ2-Cϵ4 fragment have been determined (Garman et al., Nature 2000(406):259-266, and Wan et al., Nature Immunology, 2002(3):681-686).

In the last few years, the three-dimensional structures for a large number of different allergens have been determined. Structurally, these allergens vary considerably, and no common structural motif that could explain the capability of allergens to cause the production of IgE antibodies has been identified. However, there are studies implicating that allergenicity is restricted to only a few protein families, thus raising evidence that structural features of proteins could also have a role in allergenicity (Jenkins et al., J. Allergy Clin. Immunol. 2005(115):163-170; Raudauer et al., J Allergy Clin Immunol. 2008(121):847-852; Rouvinen et al., PloS ONE 2010(5):e9037).

The essential question when studying allergenicity involves the so-called B-cell epitope, the IgE antibody-binding site of an allergen. Unfortunately, however, this B-cell epitope cannot be deduced directly from the three-dimensional structure of an allergen. Additionally, there are differences in the epitopes of a defined allergen recognized by individual patient' IgE. Therefore, B-cell epitopes have been sought using various techniques and various basis, such as by analyzing allergenic fragments or peptides, which react with polyclonal IgE serum pools from allergic patients, site-directed mutagenesis of allergens, use of epitope mimics (mimotopes) and bioinformatics modeling studies. However, as yet, no general maps of dominating epitopes exist for any allergen.

With regard to birch pollen, for instance, Holm et al. (The Journal of Immunology 2004 (173): 5258-5267) produced Bet v 1 mutants containing 4 and 9 point mutants with the aim to manipulate surface topology in "selected areas". The paper does not describe how this "selection" has been made. The mutants with four amino acid substitutions represented three different areas on the molecular surface and the mutants with nine amino acid substitutions represented five different areas on the molecular surface. These Bet v 1 mutants had in some cases reduced capacity to bind human serum IgE and to trigger human basophile histamine release. They were also able to induce IgG antibodies against unmutated Bet v 1.

Further modified recombinant allergens have been reported:

International patent publications WO 02/40676 and WO 03/096869 disclose numerous mutant forms of birch pollen allergen Bet v 1. These mutants were produced by introducing random mutations in the putative IgE binding site, based on sequence analysis of conserved surface structures of the Bet v 1 polypeptide. WO 03/096869 discloses the use of four primary mutations on different "small groups" on the allergen surface.

International patent publication WO 2007/073907 discloses a Bet v 1 polypeptide comprising three amino acid substitutions or deletions at amino acid sites 54, 115 or 123. There is no evidence that these mutants have reduced histamine release capacity.

International patent publication WO 2009/024208 discloses a Bet v 1 mutant having at least four mutations in the area amino acids 100-125. However, due to the mutations the tree-dimensional structure of the polypeptide is lost, and there is no reported histamine release activity.

International patent publication WO 2008/092992 discloses a method of blocking the type I surface interaction of allergenic substances by modifying amino acid residues on non-continuous allergenic epitopes, i.e., on a planar surface with an area of 600-900 Å on the allergenic substance and suggests that hypoallergenic birch pollen proteins could be prepared accordingly.

Niemi et al., Structure 2007(15): 1413-21, disclose one approach in the search of specific allergen epitopes in the line with the disclosure of Laver et al., Cell 1990(61):553-556, who state that the only rational method by which to determine the complete epitope of any allergen involves measuring crystal structure of an allergen in complex with an IgE antibody. Niemi et al. disclose the crystal structure of an IgE Fab fragment in complex with β-lactoglobulin (BLG). They also show how two IgE/Fab molecules bind the dimeric BLG and that the IgE epitope is different when compared to known IgG epitope structures, being a "flat" surface located in the β sheet region.

Rouvinen et al., PloS ONE 2010(5):e9037 investigated the role of dimeric structures of allergens using bioinformatics methods combined with native mass spectrometry.

(Electrospray Ionization Fourier Transform Ion Cyclotron Mass Spectrometry, ESI FT-ICR-MS). The ESI-MS measurements of the 55 known crystal structures of allergens showed that 80% of them exist in symmetric dimers or oligomers in crystals and that the majority is transient dimers that are formed at high protein concentrations. The possible relationship between dimeric structure and allergenicity was studied with a recombinant allergen from cow's milk, β-lactoglobulin (rBos d 5 B), which occurs as a dimer, and its mutant H146P, which occurs mainly as a monomer. A somewhat reduced histamine releasing capacity was observed with the monomeric rBos d 5 B mutant H146P when compared to the native Bos d 5 B and recombinant Bos d 5 B. Although the authors conclude that dimerization could be a very common and essential feature for allergens and generally suggest that the preparation of purely monomeric variants of allergens could open up novel possibilities for specific immunotherapy, the ultimate role of structural features in allergenicity remain unknown. From the in vitro crystal analysis direct conclusions as to how the allergen molecules behave in a human body, i.e. in vivo, cannot be drawn.

Today the trend in the treatment of all allergic symptoms is towards an active induction of tolerance using allergen-specific desensitization instead of avoiding the allergen, which is often not possible, or merely treating the symptoms. Current desensitization therapy is based on allergens purified from natural sources, wherein batch to batch variations may lead to problems related to finding and maintaining the right dosage and efficiency of the treatment. These problems may lead to a potential risk of anaphylactic side effects and sensitization to new allergens.

The use of recombinant allergens for desensitizing would remove the disadvantages related to batch to batch variations, and the first recombinant allergens are in clinical trials (Valenta et al., Annu Rev Immunol 2010(28):211-41). The efficiency of such allergens in the clinic thus remains to be seen.

There is a recognized and large need for safe and efficient vaccines and therapy products to meet the increasing medical problem of allergy. At present the market for safe and efficient therapies of allergy is underdeveloped.

BRIEF DESCRIPTION OF THE INVENTION

The present invention relates to a recombinant hypoallergenic birch pollen Bet v 1 polypeptide based on a wild type amino acid sequence template as depicted in SEQ ID NO: 3 or of any other Bet v 1 wild type isoform thereof, said polypeptide either naturally or by mutation comprising (1) at least one first amino acid substitution at a position selected from the group consisting of amino acid residues E101, K80, N82, S84, S99, S117, and K119, and (2) at least one second amino acid substitution at a position selected from the group consisting of amino acid residues N28, D25, N43, G46, N47, and Y158.

The present invention further relates to a hypoallergenic polypeptide defined above for use as a vaccine for desensitizing against birch pollen.

The present invention further relates to a vaccine composition comprising at least one hypoallergenic polypeptide defined above and at least one pharmaceutically acceptable adjuvant. In one embodiment of the present invention said vaccine is for sublingual administration.

The present invention further relates to a method of vaccinating against birch pollen allergy, said method comprising administering to a subject suffering from birch pollen allergy a hypoallergenic polypeptide or a vaccine composition defined above in an amount effective for desensitizing and for inducing the production of protective antibodies against birch pollen.

The hypoallergenic polypeptides according to the present invention have a histamine release capacity which is at least 20× reduced when compared to the histamine release capacity of the Bet v 1 wild type. In one embodiment the polypeptides have a histamine release capacity which is reduced at least 100×.

BRIEF DESCRIPTION OF THE FIGURES

The patent or application file contains at least one color drawing. Copies of this patent or patent application publication with color drawing will be provided by the USPTO upon request and payment of the necessary fee.

In the following the invention will be described in greater detail by means of preferred embodiments with reference to the attached drawings, in which

FIG. 4 shows the nucleic acid sequences of the Bet v 1 wild type polypeptide (A, SEQ ID NO:1) and the N28K-E101K polypeptide (B, SEQ ID NO:2) used in Example 2;

DETAILED DESCRIPTION OF THE INVENTION

Figure 1:
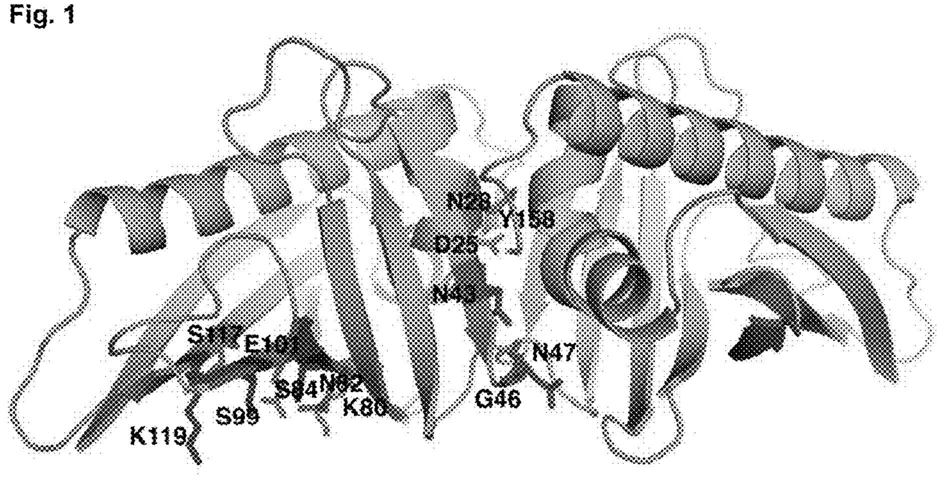
FIG. 1 illustrates the putative IgE epitope residues of Bet v1 (residues in red) and putative residues involved in the dimerisation of Bet v 1 (residues in violet) derived in Example 1.

In the following description, examples and claims both three-letter and one-letter codes are used for amino acids. See, for instance, IUPAC-IUB Joint Commission on Biochemical Nomenclature. Nomenclature and Symbolism for Amino Acids and Peptides. Eur. J. Biochem. 138:9-37 (1984).

The denomination of amino acid sites in the polypeptides according to the present invention are exemplified as follows: N28 means that there is an asparagine residue at position 28, whereas N28K means that the asparagine residue at position 28 has been replaced by a lysine residue. Correspondingly, E101 means that there is a glutamic acid residue at position 101, whereas E101K means that the glutamic acid residue at position 101 has been replaced by a lysine residue, etc.

Birch pollen allergy is a very common form of allergy and pollen of the white birch (*Betula verrucosa*) is one of the main causes of Type I allergy reactions in Europe and North America. It is estimated that about 10-15% of the population may suffer from birch pollen allergy. Furthermore, other allergens, such as apple allergens, cross-react with birch pollen specific IgE causing allergic reactions even when the subject is not subjected to pollen.

Bet v 1 is the major allergen of birch pollen and it is responsible for the IgE binding in more than 95% of birch pollen allergic subjects. Bet v 1 is a protein having a molecular weight of 17 kD. The amino acid sequence of wild type Bet v 1 is given in SEQ ID NO: 3. The WHO allergen website (www.allergen.org) lists thirty-six (36) isoforms of Bet v 1, which have been sequence aligned in FIG. 3. The alignment shows that Bet v 1 is highly conserved. The template of the isoform used as a wild-type Bet v 1 in the present invention is from isoform Bet v 1a (Bet v 1.0101), but any one of these isoallergens may be used, as appropriate, to provide a hypoallergenic polypeptide variant according to the present invention.

The amino acid sequences of all 36 Bet v 1 isoforms are disclosed in the sequence listing, as follows: 1.0101 (SEQ ID NO: 3), 1.0102 (SEQ ID NO: 4), 1.0103 (SEQ ID NO: 5), 1.2501 (SEQ ID NO: 6), 1.1501 (SEQ ID NO: 7), 1.1502 (SEQ ID NO: 8), 1.2801 (SEQ ID NO: 9), 1.3001 (SEQ ID NO: 10), 1.2901 (SEQ ID NO: 11), 1.2301 (SEQ ID NO: 12), 1.0501 (SEQ ID NO: 13), 1.0601 (SEQ ID NO: 14), 1.0602 (SEQ ID NO: 15), 1.0801 (SEQ ID NO: 16), 1.1701 (SEQ ID NO: 17), 1.0401 (SEQ ID NO: 18), 1.0402 (SEQ ID NO: 19), 1.0701 (SEQ ID NO: 20), 1.1001 (SEQ ID NO: 21), 1.2401 (SEQ ID NO: 22), 1.2601 (SEQ ID NO: 23), 1.2701 (SEQ ID NO: 24), 1.2201 (SEQ ID NO: 25), 1.0201 (SEQ ID NO: 26), 1.0901 (SEQ ID NO: 27), 1.0301 (SEQ ID NO: 28), 1.1401 (SEQ ID NO: 29), 1.1402 (SEQ ID NO: 30), 1.1901 (SEQ ID NO: 31), 1.2001 (SEQ ID NO: 32), 1.1801 (SEQ ID NO: 33), 1.1101 (SEQ ID NO: 34), 1.1201 (SEQ ID NO: 35), 1.1601 (SEQ ID NO: 36), 1.2101 (SEQ ID NO: 37), and 1.1301 (SEQ ID NO: 38), respectively.

The isoforms of Bet v 1 include variants which have different allergenic potential. The isoforms of Bet v 1 are at least 94% identical to Bet v 1 wild type amino acid sequence of SEQ ID NO: 3. For instance, isoforms Bet v 1.0401 with 96% amino acid residue identity and Bet v 1.1001 with 94% residue identity to Bet v 1.0101 have been identified as natural hypoallergens, because they were poor inducers of a mediator release. As compared to Bet v 1.0101, Bet v 1.1001 contains, e.g., the N28K mutation. They have also been regarded to fulfill the criteria to represent excellent vaccine candidates. (Wagner et al., J. Allergy Clin Immunol 2008; 121:725-735). However, no scientific, experimental or clinical data is available.

The present invention provides mutated hypoallergenic polypeptide variants of Bet v 1, which are useful as vaccines for immunizing subjects in need thereof and thus preventing and/or alleviating allergy and desensitizing subjects suffering from allergy against birch pollen.

The recombinant birch pollen Bet v 1 polypeptides according to the present invention have a wild type amino acid sequence, but they contain mutations at selected amino acid positions to reduce or fully diminish their ability to induce the production of IgE but to retain their capacity to induce the production of protective IgG antibodies, i.e., they are hypoallergenic.

Specifically, the present invention relates to a recombinant hypoallergenic birch pollen Bet v 1 polypeptide based on a wild type amino acid sequence template as depicted in SEQ ID NO: 3 or of any other Bet v 1 wild type isoform thereof, said polypeptide either naturally or by mutation comprising (1) at least one first amino acid substitution at a position selected from the group consisting of amino acid residues E101, K80, N82, S84, S99, S117, and K119, and (2) at least one second amino acid substitution at a position selected from the group consisting of amino acid residues N28, D25, N43, G46, N47, and Y158.

In one embodiment, the polypeptide of the present invention has the template of a wild type amino acid sequence as depicted in SEQ ID NO: 3. In another embodiment, the polypeptide of the present invention has the template of a wild type amino acid sequence selected from the group consisting of SEQ ID NO: 4-38.

In one embodiment of the invention, the recombinant hypoallergenic birch pollen Bet v 1 polypeptide is represented by the amino acid sequence depicted in SEQ ID NO:39. SEQ ID NO: 39 discloses Bet v 1 polypeptide sequence with positions for amino acid substitutions (amino acid positions 25, 28, 43, 46, 47, 80, 82, 84, 99, 101, 117, 119, 158) and also discloses wild type amino acids at these positions.

Any combination of first and second substitutions at any depicted positions results in a hypoallergenic polypeptide. In one embodiment of the invention, the polypeptide comprises an amino acid sequence selected from the group consisting of SEQ ID NO: 41-47, and at least one second amino acid substitution at a position selected from the group consisting of amino acid residues N28, D25, N43, G46, N47, and Y158, or isoform thereof. Preferably, the polypeptide has an amino acid sequence selected from the group consisting of SEQ ID NO: 41-47, and at least one second amino acid substitution at a position selected from the group consisting of amino acid residues N28, D25, N43, G46, N47, and Y158, or isoform thereof. In another embodiment of the invention, the polypeptide comprises an amino acid sequence selected from the group consisting of SEQ ID NO: 41, wherein amino acid 101 is K, SEQ ID NO: 42, wherein amino acid 80 is Y, SEQ ID NO: 43, wherein amino acid 82 is K, SEQ ID NO: 44, wherein amino acid 84 is K, SEQ ID NO: 45, wherein amino acid 99 is K, SEQ ID NO: 46, wherein amino acid 117 is K, and SEQ ID NO: 47, wherein amino acid 119 is E; and at least one second amino acid substitution at a position selected from the group consisting of amino acid residues N28, D25, N43, G46, N47, and Y158. Preferably the polypeptide has an amino acid sequence selected from the group consisting of SEQ ID NO: 41, wherein amino acid 101 is K, SEQ ID NO: 42, wherein amino acid 80 is Y, SEQ ID NO: 43, wherein amino acid 82 is K, SEQ ID NO: 44, wherein amino acid 84 is K, SEQ ID NO: 45, wherein amino acid 99 is K, SEQ ID NO: 46, wherein amino acid 117 is K, and SEQ ID NO: 47, wherein amino acid 119 is E; and at least one second amino acid substitution at a position selected from the group consisting of amino acid residues N28, D25, N43, G46, N47, and Y158. SEQ ID NO: 41 discloses Bet v 1 polypeptide sequence, wherein amino acid at position 101 is a substitution and not wild type amino acid E. Similarly SEQ ID NOs: 42-47 show Bet v 1 polypeptides, wherein amino acids at positions 80, 82, 84, 99, 117 and 119, respectively, are substitutions and not wild type amino acids.

In one embodiment of the invention, said at least one first amino acid substitution is at a position selected from the group consisting of amino acid residues E101 and S99, and said at least one second amino acid substitution is at a position selected from the group consisting of amino acid substitutions N28 and D25.

In yet another preferred embodiment of the invention said at least one first amino acid substitution is at position E101, and said at least one second amino acid substitution is at position N28. In one preferred embodiment of the invention, the recombinant hypoallergenic birch pollen Bet v 1 polypeptide is represented by the amino acid sequence depicted in SEQ ID NO:40. SEQ ID NO: 40 shows Bet v 1 polypeptide sequence with substitutions at positions 28 and 101, amino acids at these positions being lysines (K).

The hypoallergenic polypeptide variants of the present invention comprise also variants, which contain more than one first and second substitution. The terms “at least one first substitution” and “at least one second substitution” mean that said first and second substitutions may each comprise one, two, three or four or more substitutions, and any combinations of first and second substitutions are possible, as long as the ability of the hypoallergenic Bet v 1 polypeptide to induce protective antibody response retains. Thus in one preferred embodiment of the invention the first amino acid substitution comprises substitution at position E101, and said second amino acid substitutions are at positions N28 and D25 or at positions N28, D25 and Y158. In another preferred embodiment of the invention first amino acid substitution comprises substitutions at positions E101 and S99 and said second amino acid substitution is at position N28. In yet another preferred embodiment of the invention said first amino acid substitutions are at positions E101 and S99, and said second amino acid substitutions are at positions N28 and D25.

In a further preferred embodiment of the invention, the substitutions of Bet v 1 are at least E101 and N28, E101 and D25, E101 and N43, E101 and G46, E101 and N47, E101 and Y158, K80 and N28, K80 and D25, K80 and N43, K80 and G46, K80 and N47, K80 and Y158, N82 and N28, N82 and D25, N82 and N43, N82 and G46, N82 and N47, N82 and Y158, S84 and N28, S84 and D25, S84 and N43, S84 and G46, S84 and N47, S84 and Y158, S99 and N28, S99 and D25, S99 and N43, S99 and G46, S99 and N47, S99 and Y158, S117 and N28, S117 and D25, S117 and N43, S117 and G46, S117 and N47, S117 and Y158, K119 and N28, K119 and D25, K119 and N43, K119 and G46, K119 and N47 or K119 and Y158. In a further preferred embodiment of the invention, the substitutions are one of these combinations.

In one preferred embodiment of the invention, there are altogether at least two, three or four amino acid substitutions. Preferably, the polypeptide of the invention has two, three, four, five, six, seven, eight, nine or ten substitutions. More preferably, the polypeptide has two, three or four substitutions. One of the advantages of the invention is that only a small number of substitutions (at least two) are needed for the desired effects.

The polypeptides according to the present invention are hypoallergenic, and exhibit a histamine release capacity which is at least 20×, preferably 100×, reduced when compared to the histamine release capacity of the corresponding unmutated Bet v 1 wild type.

The hypoallergenic polypeptides according to the present invention are useful as vaccines against allergy, especially birch pollen allergy. Vaccines comprising polypeptides according to the present invention are formulated according to standard pharmaceutical procedures known to skilled persons in the art. Vaccines according to the present invention are especially suited for sublingual administration.

Hypoallergenic variants according to the present invention are obtained by mutating chosen specific amino acid residues, e.g., residues with bulky side chains, located on the epitope surfaces of Bet v 1. The selected amino acid residues are those, whose side chains point outside towards the solvent. Mutating such residues cause minimal change to the basic 3-dimensional structure of the allergen. Preferably, however, the mutagenesis modifies the surface of the epitope to such an extent that the binding and cross-linking of IgE antibodies on the mast cell surface is prevented or strongly reduced, while the over-all structure of the variant is still very similar to that of the wild type allergen. Such a mutation favors the induction of IgG and other protective antibodies, having the ability of binding both to the wild-type allergen and to the mutated variant allergen. The effect of the mutation is determined as a lower affinity of the allergen specific IgE antibody towards the modified Bet v 1 allergen. Preferably the mutation decreases the affinity of the specific IgE antibody at least tenfold, preferably at least 20-fold, and more preferably 20- to 100-fold, and most preferably more than 100-fold. The resulting modified Bet v 1 allergen can be used to evoke tolerance against birch pollen in allergic patients.

The hypoallergenic variant polypeptides according to the present invention, useful in allergen-specific desensitization, possess two features: 1) the ability to strongly reduce an IgE-mediated reaction; and 2) a retained wild-type 3D folding, and thus the capability of inducing the production of IgG-antibodies capable to bind wild type allergen.

The knowledge of the structure of the IgE binding epitope would greatly simplify the design of hypoallergenic variants, as mentioned above. However, the structure of Bet v 1 complexed with IgE antibody is unfortunately not available. It is not known how much there are differences in the epitopes of a defined allergen recognized by individual patient' IgE. The use of peptides in the epitope scanning is also unreliable and actually useful only when scanning linear epitopes (Niemi et al., Structure 2007(15): 1413-21). The conformation as well as the physical properties, e.g., solubility, of a single peptide may differ markedly from those of corresponding portion of a polypeptide chain forming part of a native protein structure. Therefore, the design of the mutant Bet v 1 allergens was based on molecular surface analysis using molecular graphics programs, such as PyMOL, to elucidate the structure of the epitope and to test potential hits by preparing and testing the mutants. In addition, the ability of dimerization of Bet v 1 was taken into account in the design.

The crystal structure of Bet v 1 (protein data bank code 1 BV1) was used to define the quaternary structure of Bet v 1. The PDBePISA internet server was used for creating coordinates for the symmetric dimer of Bet v 1. It has been estimated that the distance between IgE antibodies in the cluster on the mast cell surface is about 5 nm (Knol, E F; Mol. Nutr. Res. 50 (2006):620). By studying the molecular surface of the Bet v 1 dimer around the two-fold symmetry axis within a distance of 2.5 nm from the symmetry axis, two putative epitopes were identified on the molecular surface of Bet v 1 (FIG. 1).

The putative epitope is composed of amino acid residues V2-E6; R70-D75; N78-S84; E96-K103; and K115-H121, whereas monomer-monomer interface of Bet v 1 dimer is composed of amino acid residues K20-K32; S39-P50; V74-H76; and D156-N159.

These putative epitopes were carefully analyzed, in order to identify amino acid residues, which could serve as mutation points. Preferred mutations points should have the ability to decrease the binding of the allergen to IgE antibodies but still maintain the three-dimensional structure of the wild-type allergen. The putative epitope includes amino acid residues K80, N82, S84, S99, E101, S117, and K119. The monomer-monomer interface includes residues D25, N28, N43, G46, N47, and Y158. The residues E101 and N28 were considered as the most interesting mutation points, as they are located in the center of the putative epitope and in a strategic position on the monomer-monomer interface, respectively. In the present invention the first amino acid substitution(s) is(are) in the epitope area and the second amino acid substitution(s) is(are) in the monomer-monomer-interface.

Figure 3:
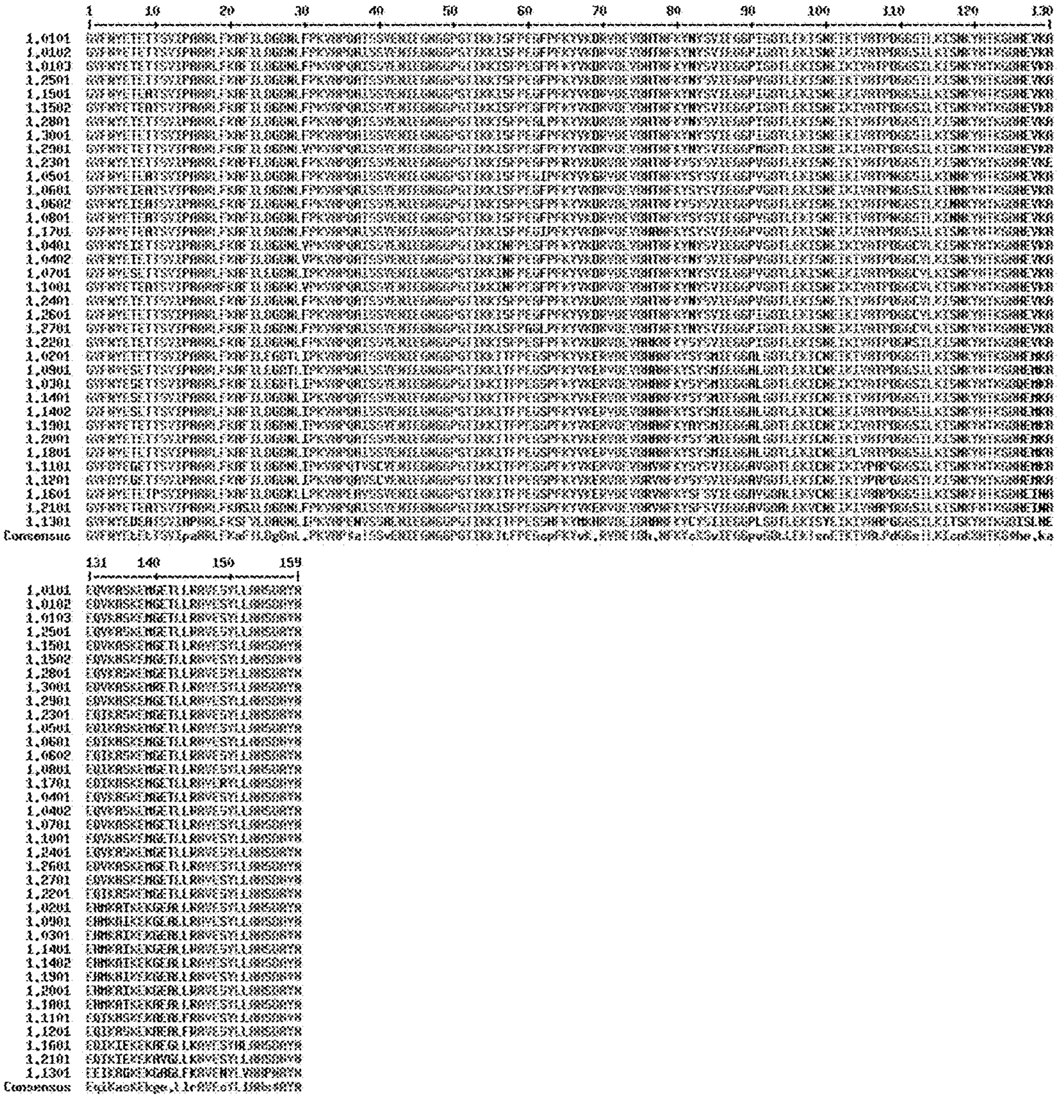
FIG. 3 is an amino acid sequence alignment of 36 isoforms of Bet v 1.

These two residues are highly conserved in all 36 isoforms of Bet v 1. No natural variation exists in residue 101. The natural variations are found in residue 28, which exists as asparagine (in 31 isoforms), lysine (in 2 isoforms) or tyrosine (in 3 isoforms). Residues D25, N43, G46, N47, K80, S84, K119, and Y158 are conserved, whereas residues N82, S99, and S117 vary slightly, as shown in FIG. 3.

The next step was to select an appropriate mutation for each residue. As an example, S99 is a small hydrophilic and neutral amino acid residue. The mutation which would interfere IgE binding would thus be of "opposite" nature, i.e., large and/or charged, for example Ser to Lys, Arg, Asp, Tyr, and Val. Similarly, E101 and N28 can be replaced by a residue with the opposite charge (Lys, Arg) or with a hydrophobic residue (Tyr, Ile, or Trp). Substitutions at residues D25, N43, G46, N47, K80, N82, S84, S117, and K119 could be designed correspondingly. Table 1 lists potential substitutions, which would yield Bet v 1 hypoallergenic mutants according to the present invention set forth in SEQ ID NO: 39.

stability of the vaccine, in terms of safety and reproducibility. The patients need to be strictly monitored, often hospitalized, after each injection.

As the histamine release capacity of the hypoallergens according to the present invention is substantially reduced, the dosing-up phase could be significantly shorter than that of a conventional allergy vaccination, or at best no dosing-up scheme could be needed. Modified, recombinant hypoallergens according to the present invention do not present any batch-to-batch variation. Thus, close monitoring of the dose-response and possible side-reactions is not needed.

Thus, the present invention further relates to a use of a hypoallergenic Bet v 1 polypeptide described in detail above as a vaccine and to a vaccine composition comprising at least one recombinant hypoallergenic Bet v 1 polypeptide of the invention and at least one pharmaceutically acceptable diluent or adjuvant, such as saline, buffer, aluminum hydroxide and like. The present invention further relates to a method of vaccinating against birch pollen allergy, said method comprising administering to a subject suffering from birch pollen allergy a hypoallergenic polypeptide or a vaccine composition as defined above in an amount and using a vaccination schedule effective for inducing the production of protective antibodies against birch pollen.

A "subject" of vaccination is a human (adult, child or adolescent) or an animal. Preferably, the animal is any domestic animal such as a dog, cat, horse, cow, sheep or pig.

TABLE 1

| | Mutants of Bet v 1 wt | | | | |
|---|---|---|---|---|---|
| Bet v 1 wt | mutant 1 | mutant 2 | mutant 3 | mutant 4 | mutant 5 |
| EPITOPE MUTANTS | | | | | |
| S99 small hydrophilic | K large charged | R large charged | D charged | Y large hydrophobic | V large hydrophobic |
| E101 charged | K large oppositely charged | R large oppositely charged | Y large hydrophobic | I large hydrophobic | W large hydrophobic |
| K80 charged | Y large hydrophobic | E oppositely charged | W large hydrophobic | I large hydrophobic | L large hydrophobic |
| S84 small hydrophilic | K large charged | R large charged | D charged | E charged | Y large hydrophobic |
| N82 hydrophilic | K large charged | R large charged | Y large hydrophobic | E charged | L hydrophobic |
| S117 small hydrophilic | K large charged | R large charged | D charged | Y large hydrophobic | L large hydrophobic |
| K119 charged | E oppositely charged | Y hydrophobic | L hydrophobic | W hydrophobic | I hydrophobic |
| MONOMER MUTANTS | | | | | |
| D25 charged | K large oppositely charged | R large oppositely charged | Y large hydrophobic | H large charged | L large hydrophobic |
| N28 hydrophilic | K large charged | R large charged | Y large hydrophobic | I large hydrophobic | W large hydrophobic |
| N43 hydrophilic | Y large hydrophobic | H large charged | I large hydrophobic | L large hydrophobic | E charged |
| G46 no side chain | P main chain | V hydrophobic | D charged | T hydrophilic | L hydrophobic |
| N47 hydrophilic | E large charged | L hydrophobic | I hydrophobic | Y large hydrophobic | P main chain |
| Y158 large hydrophobic | D charged | E charged | L hydrophobic | P main chain | I hydrophobic |

Segments: V2-E6; R70-D75; N78-S84; E96-K103; K115-H121

The modified Bet v 1 hypoallergens according to the present invention are useful as vaccines. Conventional allergy vaccination is typically carried out as multiple subcutaneous immunizations over an extended time period, e.g., one to two years. In order to minimize the risk of anaphylactic reactions, the immunization scheme is applied in two phases, an initial up-dosing phase and a maintenance phase. The up-dosing phase starts with minute doses, which are then slowly increased, typically over a 16-week period until the maintenance dose is reached. The maintenance phase typically comprises injections every sixth week. Such a vaccination regime is tedious for the patient, requiring a long-term commitment. Moreover, it puts high impact on the For instance, a hypoallergen according to the present invention is formulated as conventional vaccine formulations, such as aluminum hydroxideadsorbed vaccines, using methods well known in the art (Niederberger et al., PNAS, 101(2):14677-82, 2004). Alternatively and preferably, however, the hypoallergens according to the present invention may be administered by other suitable vaccination routes and schemes, such as oromucosal or sublingual administration, using methods and formulations known in the art. See, e.g., European Patent publication EP 1812059.

The modified Bet v 1 hypoallergens could be used in concentrations of, e.g., 0.5 μg/ml, 5 μg/ml or 50 μg/ml. Exemplary doses may vary between 0.05 μg and 2 μg during a possible dosing-up phase, and between 3-15 μg during the maintenance phase, preferably 5-15 μg, most preferably about 10 μg, depending on the severity of the allergy, the age and medical history of the patient. A suitable dose is easily decided by a clinician familiar with treating and preventing allergy.

International patent publication WO04/047794 discloses a solid fastdispersing dosage form for sublingual administration of an allergy vaccine, and US patent application 2009/0297564 discloses a liquid vaccine formulation for oromucosal administration.

The modified Bet v 1 hypoallergens according to the present invention are particularly suitable for sublingual administration using sublingual drops. For this purpose the hypoallergenic polypeptides are provided in saline. A safe and effective dose range for administration of the polypeptides, as well as the dosing regimen capable of eliciting a desired immune response is determined during clinical development of the vaccine candidates according to the present invention, using methods and schemes known in the art.

A maximum tolerated single dose of a hypoallergen according to the present invention is determined in a study in allergic male and female subjects, which are exposed to increasing sublingual doses. When the maximal tolerated dose of predefined dose is reached, the study is adapted to a dose ranging study with daily dosing, where the dose levels differ by a factor of 2 to 4. The initial dose is in the range of 10-100 μg, and the study provides the maximal tolerated sublingual dose, which may be as high as 20 mg.

Thereafter dose escalation and dose ranging over a wide dose range administered daily or weekly are studied. The safety of the vaccination dose range is preliminary tested with a Skin Prick Test prior to administering multiple doses. These studies provide primarily immunological parameters, and secondarily, eventual efficacy after challenge by birch pollen.

The hypoallergenic polypeptide vaccines according to the present invention should elicit a T-cell response detectable as a shift from TH2- to TH1-type. Production of IgG antibodies should be demonstrable before entering allergenic challenge testing.

Finally, a study in allergic patients is performed, as a double blind, randomized placebo controlled desensitization study in allergic male and female subjects exposed to a number of sublingual doses during 3-6 months, with a follow up for 12 months initially. The subjects will be challenged by allergen prior to the start of the study as well as every six months thereafter in a double blind manner.

The study will show a statistically and clinically significant difference between the groups receiving placebo and a hypoallergen vaccine according to the present invention, when they are challenged to the native allergen.

EXAMPLES

The following examples are given to further illustrate embodiments of the present invention, but are not intended to limit the scope of the invention. It will be obvious to a person skilled in the art, as technology advances, that the inventive concept can be implemented in various ways. The invention and its embodiments are thus not limited to the examples described herein, but may vary within the scope of the claims.

Example 1

Design of the Bet v 1 Mutations

The goal in the hypoallergen design is to achieve a mutant allergen whose ability to bind and cross-link IgE-antibodies on the mast-cell surface is strongly reduced but which still maintains a very similar structure as the wild type allergen. This would favor the induction of IgG and other antibodies which would have ability to bind both to wild-type allergen and mutant allergen.

The knowledge of the IgE epitope would greatly simplify design. However, there is no structure of Bet v 1 complexed with the IgE antibody available. The use of peptides in the epitope scanning is also unreliable (Niemi et al., Structure (15):1413-21, 2007). The only method to suggest an epitope is to study the molecular surface of Bet v 1 allergen and test the possible hit by preparing mutants. Firstly, we identified a putative epitope (FIG. 1) on the molecular surface of Bet v 1. Secondly, we selected such residues on this putative epitope which as mutated would maintain a three-dimensional structure similar to the wild-type allergen and still have the ability to decrease binding to IgE antibodies. The putative epitope includes amino acid residues K80, N82, S84, S99, E101, S117, and K119.

The third step is to select mutation for each residue. As an example, S99 is a small hydrophilic and neutral residue, serine. The mutation which would interfere IgE binding would thus be "opposite", i.e., large and/or charged, for example S99K (serine to lysine), S99R (serine to arginine), S99D (serine to aspartic acid), S99Y (serine to tyrosine), and S99V (serine to valine). In the case of E101, mutations interfering with the IgE binding could include using residues with an opposite charge (Lys, Arg) or using hydrophobic residues (Tyr, Ile, Trp).

Finally, to introduce the feature of prohibiting dimerisation into the polypeptide variants of the invention monomer a mutation design, based on crystal structure of Bet v 1 (PDB code 1 BV1), was used. The model for Bet v 1 dimer was created with the PISA server. The monomer-monomer interface was studied by using molecular graphics program. The mutants were designed on this interface using the same principle as used in the epitope mutants. As an example, N28 on the monomer-monomer interface is a medium-sized hydrophilic residue. The mutation, which interferes the dimer formation, would thus be a very large charged (lysine, arginine) or hydrophobic residue (tyrosine, isoleusine, tryptophane).

Example 2

Cloning of the Recombinant Bet v 1 Molecules

Figure 2:
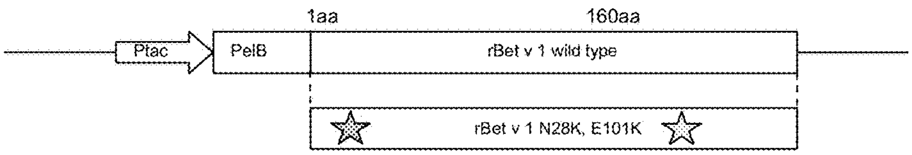
FIG. 2 is a schematic presentation of the bacterial expression units for production of recombinant allergens, wherein Ptac is a promoter, PelB is the signal sequence linked to the coding region of recombinant allergens and the stars illustrate the amino acid substitution sites.

To produce the wild type (wt) and the mutant of the recombinant Bet v 1 molecules (rBet v 1) the cDNAs encoding these particular proteins were cloned into a bacterial expression plasmid (FIG. 2). First, the rBet v 1 cDNAs designed in Example 1, with the codon optimization for *Escherichia coli* production in vector pUC57 (wt and N28K-E101K) were ordered from GenScript Corporation (USA). The cDNAs contained NcoI restriction site at the 5'end and HindIII at the 3'end. The cDNAs were cloned as NcoI-HindIII fragments into bacterial expression vector pKKtac encoding the Ervinia carotovora's pectate lyase (pelB) signal sequence (Takkinen et al., Protein Eng. (4): 837-841, 1991) and expression plasmids were transformed into *E. coli* XL-1 Blue strain. The DNA sequences of the rBet v 1 and the N28K-E101K mutant were verified by DNA sequencing (ABI 3100 Genetic Analyzer, Applied Biosystems), and are herein depicted as SEQ ID NO:s 1-2.

Example 3

Production of the Recombinant Bet v 1 Molecules

The expression vector of wild type rBet v 1 was transformed into *E. coli* BL21 DE strain and the expression vector Bet v 1 N28K-E101K mutant into *E. coli* RV308 strain for bacterial expression. Single colonies of rBet v 1 wt and Bet v 1 N28K-E101K mutant were inoculated into 5 ml SB or TB, 100 μg/ml ampicillin and 1% glucose, respectively, and cultivated for 16 h at +37° C. with 220 rpm shaking. Cultivations were 1:50 diluted into 3×300 ml SB or TB with 100 μg/ml ampicillin and cultivated at +37° C. until the OD600 reached 4. Protein expression was induced by the addition of IPTG to a final concentration of 1 mM, and the cells were cultivated for 16 h at RT with 170 rpm shaking. Cells were harvested by centrifugation for 15 min at 5000 g at +4° C., and the periplasmic fraction of the cells was isolated by an osmosis-shock method described by Boer et al. (Protein Expression & Purification, 2007(51): 216-226). The cell pellet equivalent of 900 ml of the culture was re-suspended in 300 ml, 30 mM Tris/HCl, 20% sucrose, pH 8.0, and 1 mM EDTA, and incubated for 20 min under shaking on ice. The suspension was centrifuged for 20 min at 8000 g at 4° C. After this the pellet was re-suspended in 75 ml of ice-cold 5 mM $MgSO_4$ and shaken for 20 min at 4° C. on ice, and the osmotic shock fluid was harvested by centrifugation at 8000 g for 20 min at 4° C.

Example 4

Purification of the rBet v 1 Molecules

Periplasmic fractions of the wild type rBet v 1 and the N28K-E101K mutant were supplemented with 1M NaCl and the first chromatographic purification step for both expressed proteins was carried out by a phenyl-Sepharose column (GE Healthcare) with 20 mM $NaH_2PO_4$, 1M NaCl, pH 5.0 buffer using the flow rate 2 ml/min. The elution was performed with a linear gradient of 20 mM Tris-HCl, pH 9.3, with 7.5% isopropanol. Fractions containing the recombinant Bet v 1 wild type or N28K-E101K mutant were pooled and concentrated. The wild type Bet v 1 was further purified by a Bio-Gel P60 size exclusion chromatography column with a bed height of 460 mm and 1×PBS buffer with a flow rate of 0.3 ml/min. In the case of the rBet v 1 N28K-E101K mutant an additional amylose resin chromatography step was required to get rid of *E. coli* maltose binding protein contamination before the size exclusion chromatography.

The protein concentration of pooled rBet v 1 fractions was determined at 280 nm.

Example 5

Analysis of rBet v 1 and the N28K-E101K Mutant by Mass Spectrometry

Figure 7:
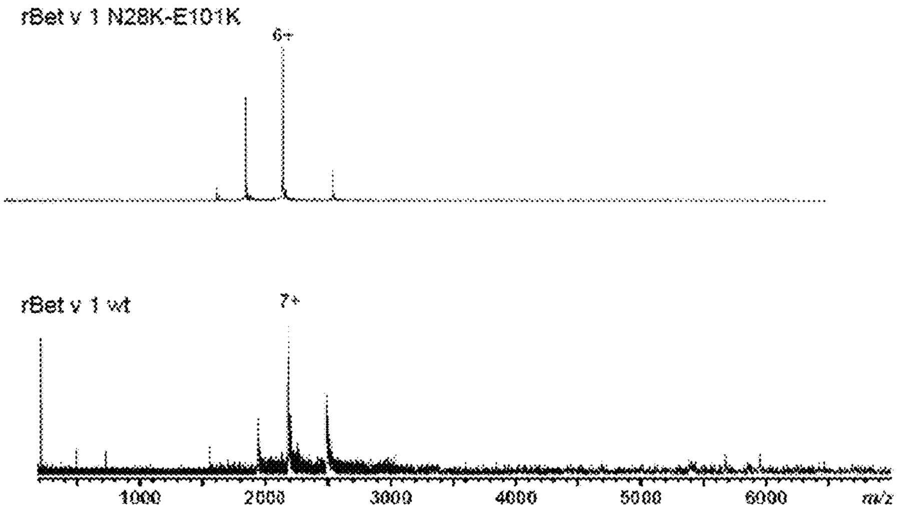
FIG. 7 shows the native ESI FT-ICR mass spectra of the recombinant Bet v 1 wild type and recombinant Bet v 1 mutant N28K-E101K at concentration of 3 μM.

Mass-spectrometric experiments were performed with a 4.7 T Bruker BioAPEX-II ESI FT-ICR mass spectrometer (Bruker Daltonics, Billerica, Mass., USA) equipped with a conventional ESI source (Apollo-II™). Native mass spectra: desalted allergen samples at concentration of 3 μM in 10 mM ammonium acetate buffer (pH 6.9) were directly infused at a flow rate of 1.5 mL/min with dry nitrogen serving as the drying (200° C., 6 mbar) and nebulizing gas. All instrumental parameters were optimized to maintain non-covalent interactions in the gas-phase and to maximize ion transmission at m/z 2000-3000. The same instrumental parameter settings were employed throughout to avoid any bias between different samples. Typically, 500-1000 co-added 128-kword time-domain transients were recorded and processed to 512-kword data prior to fast Fourier transform and magnitude calculation. Mass calibration was done externally with respect to the ions of an ES Tuning Mix (Agilent Technologies, Santa Clara, Calif., USA). Denaturated spectra were typically measured in acetonitrile/water/acetic acid solution. All data were acquired and processed with the use of Bruker XMASS 7.0.8 software. The native ESI FT-ICR mass spectra shows that the recombinant Bet v 1 mutant N28K-E101K folds similarly as the recombinant Bet v 1 wild type (FIG. 7).

Example 6

Inhibition of Serum IgE Binding to Recombinant Bet v 1 and Bet v 1 N28K-E101K Polypeptides Analyzed by a Competitive ELISA The binding of an IgE serum sample of a birch pollen allergic person (E3) to biotinylated rBet v 1 immobilized on streptavidin wells was inhibited by increasing amounts of the rBet v 1 and rBet v 1 N28K-E101K mutants. First, commercially available rBet v 1 (wild type, Biomay) was biotinylated using Sulfo-NHS-LC-biotin (Pierce) according to manufacturer's protocol. The biotinylated rBet v 1 (0.5 μg/well) was immobilized onto streptavidin (SA) wells (Roche Diagnostics Gmbh) followed by a washing step and the addition of E3 serum (1:6 dilution). After a 2-hour incubation at RT in a shaker and a washing step different amounts (4, 1, 0.25, 0.0625, 0.0156, and 0.0039 μg) of rBet v 1 were added and incubated for 2 h at RT in a shaker. After a washing step, the detection of bound IgE molecules was performed using a 1:1000 dilution of an AFOS-conjugated anti-human IgE antibody (Southern Biotech Associates Inc.) with incubation for 1 h at RT in a shaker. Finally the substrate solution, p-nitrophenylphosphate (Sigma), was added and the absorbance values at 405 nm were measured (Varioscan, Thermo Electron Corporation).

Figure 5:
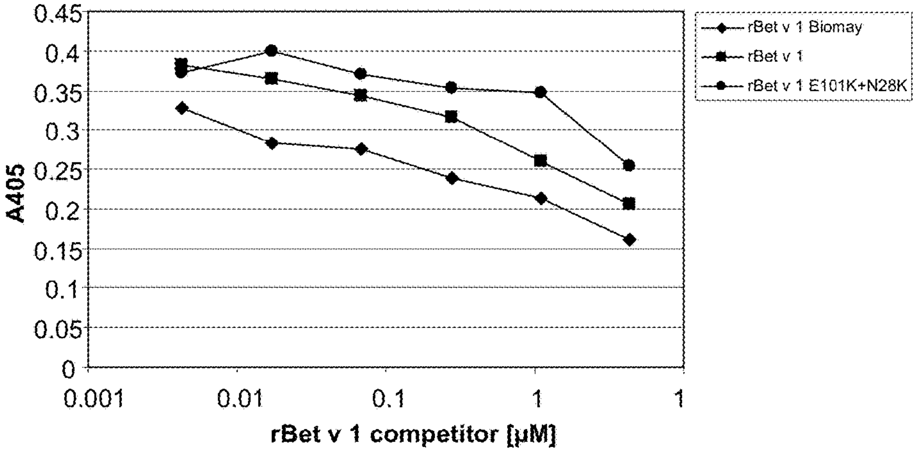
FIG. 5 shows the competitive inhibition of serum IgE binding to Bet v 1 with recombinant Bet v 1 and Bet v 1 N28K-E101K polypeptides.

The result of serum IgE binding to r Bet v 1 polypeptides analysed by a competitive ELISA is shown in FIG. 5. The rBet v 1 polypeptides, wt and N28-E101K mutant, were used for competing the binding of serum of a Bet v 1 allergic person (E3) to immobilized rBet v 1 (Biomay). Both rBet v 1 wild type molecules (a commercial one from Biomay and own product) inhibited the IgE binding to the immobilized Bet v 1. The Bet v 1 mutant N28K-E101K showed reduced inhibition when compared to the rBet v 1 controls, indicating that the mutations E101K and N28K affect the IgE epitope and dimerization of Bet v 1.

Example 7

Histamine Release Assay

The biological activity of the purified recombinant Bet v 1 polypeptides was analyzed by the method of passive sensitization of stripped basophils and a subsequent challenge with the allergen molecules. The histamine release assay was performed as an outsourced service at RefLab ApS, Copenhagen, Denmark, having an accredited histamine release assay method. The induction of the in vitro release of histamine from basophilic leukocytes by a commercial recombinant Bet v 1 (Biomay, Austria) and the two recombinant Bet v 1 proteins, wt and N28K-E101K, was measured. Each of the three allergens was tested in the passive transfer test as a dose response study with the concentration range of: 20-0.06 ng/in duplicates with the serum of a Bet v 1 allergic person (E3).

Figure 6:
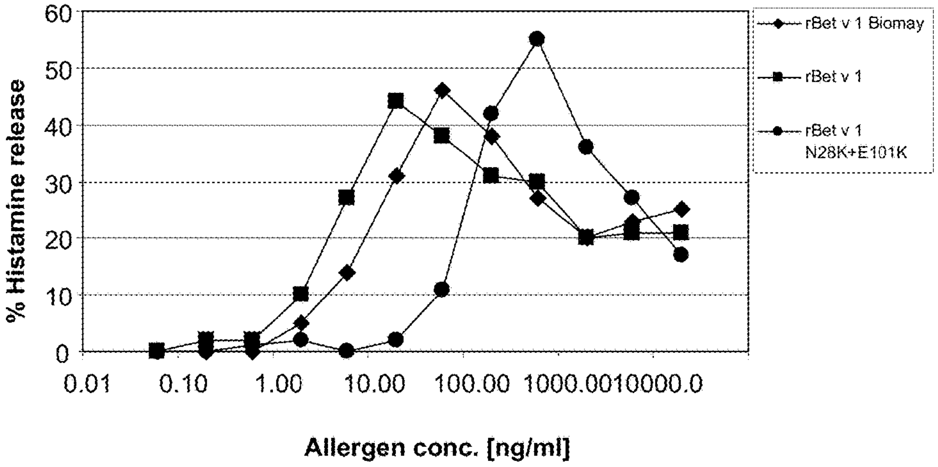
FIG. 6 shows the results of histamine release experiments with recombinant Bet v 1 and Bet v 1 N28K-E101K polypeptides.

The result of the histamine release assay is shown in FIG. 6. The rBet v 1 N28k-E101K was 100 times less biologically active compared to the reference, commercial recombinant Bet v 1 (Biomay), and rBet v 1 wild type It will be obvious to a person skilled in the art that, as the technology advances, the inventive concept can be implemented in various ways. The invention and its embodiments are not limited to the examples described above but may vary within the scope of the claims.

Example 8

Skin Prick Test

Skin prick tests (SPTs) with three voluntaries with two diagnosed birch pollen allergy and with one non-atopic person were performed with recombinant Bet v 1 polypeptides and relevant controls after the approval of the ethical committee of Helsinki University Central Hospital. The endotoxins of the recombinant Bet v 1 polypeptide preparations were removed by the Detoxi-Gel Endotoxin Removing Gel (Thermo: Cat. No. 20344) where after endotoxin content was analysed by ToxinSensor Endotoxin Detection System (GenScript: Cat. No. L00350C). The recombinant Bet v 1 polypeptide preparations were filter sterilised by Costar SPIN-X (Cat. No. 8160) and stored in aliquots at −20° C.

SPT was carried out using recombinant Bet v 1a wt (Biomay) and N28K-E101K mutant at the concentrations of 50 and 5 μg/ml and a commercial birch pollen extract (AlkAbello). Sodium chloride (0.9%) and histamine dihydrochloride (AlkAbello) served as negative and positive controls, respectively. Before pricking the skin, lancets were set in the tubes containing the skin prick reagents. The responses were measured after 15 minutes and after 6 and 20 hours. The diameter of the skin response for histamine dihydrochloride in each tested individual was 5 mm after 15 min and this value was selected as positive (+) response (Table 2). The immediate skin reactions induced by the Bet v 1 mutant N28K-E101K with the concentration of 50 μg/ml were milder when compared to the reactions induced by the Bet v 1 wt at the same concentration. The skin reactions induced by the Bet v 1 wt and N28K-E101K mutant with the concentration of 5 μg/ml were comparable. Remarkably in the case of both allergic patients the skin reactions induced by the Bet v 1 N28K-E101K mutant disappeared within a notably shorter time than compared to the Bet v 1 wt.

TABLE 2

Results of the skin prick test

| | 15 min | 6 h | 20 h |
|---|---|---|---|
| Patient 1 | | | |
| Histamine dihydrochloride (10 mg/ml) | + | + | — |
| Birch pollen extract 10HEP (AlkAbello) | + | + | — |
| rBet v 1 wt (50 μg/ml) | ++ | ++ | + |
| rBet v 1 wt (5 μg/ml) | + | + | — |
| rBet v 1 N28K + E101K (50 μg/ml) | ++ | — | — |
| rBet v 1 N28K + E101K (5 μg/ml) | + | — | — |
| Patient 2 | | | |
| Histamine dihydrochloride (10 mg/ml) | + | + | — |
| Birch pollen extract 10HEP(AlkAbello) | + | + | — |
| rBet v 1 wt (50 μg/ml) | +++ | +++ | ++ |
| rBet v 1 wt (5 μg/ml) | + | + | + |
| rBet v 1 N28K + E101K (50 μg/ml) | + | — | — |
| rBet v 1 N28K + E101K (5 μg/ml) | + | — | — |
| Non-atopic person | | | |
| Histamine dihydrochloride (10 mg/ml) | + | — | — |
| Birch pollen extract 10HEP (AlkAbello) | — | — | — |
| rBet v 1 wt (50 μg/ml) | — | — | — |
| rBet v 1 wt (5 μg/ml) | — | — | — |
| rBet v 1 N28K + E101K (50 μg/ml) | — | — | — |
| rBet v 1 N28K + E101K (5 μg/ml) | — | — | — |

+ diameter of the skin response ≥ 5 mm

++ diameter of the skin response ≥ 8 mm

+++ diameter of the skin response ≥ 11 mm

The invention claimed is:

1. A recombinant hypoallergenic birch pollen Bet v 1 polypeptide having the amino acid sequence of SEQ ID NO: 40.

2. The polypeptide according to claim 1, having a histamine release capacity which is at least 20× reduced when compared to the histamine release capacity of the wild type Bet v 1.

3. The polypeptide according to claim 2, having a histamine release capacity which is at least 100× reduced when compared to the histamine release capacity of the wild type Bet v 1.

4. A pharmaceutical composition comprising the hypoallergenic polypeptide according to claim 1 and a pharmaceutically acceptable diluent or adjuvant.

5. The composition according to claim 4, wherein the pharmacuetical composition is for sublingual administration.

6. A pharmaceutical composition, comprising:

a recombinant birch pollen Bet v 1 polypeptide having the amino acid sequence of SEQ ID NO: 40, and a pharmaceutically acceptable carrier or adjuvant suitable for use as a pharmaceutical composition.

7. A method of treating birch pollen allergy in a subject, said method comprising:

administering to the subject suffering from birch pollen allergy a hypoallergenic polypeptide according to claim 1 or a pharmaceutical composition according to claim 6 in an amount effective for desensitizing and for inducing the production of protective antibodies against birch pollen.

8. The pharmaceutical composition according to claim 6, further comprising an adjuvant.

9. The pharmaceutical composition according to claim 6, wherein the pharmaceutically acceptable carrier or adjuvant is selected from the group consisting of saline, buffer and aluminum hydroxide.

10. The pharmaceutical composition according to claim 8, wherein the adjuvant is aluminum hydroxide.

* * * * *

SEQUENCE LISTING

```
<160> NUMBER OF SEQ ID NOS: 47

<210> SEQ ID NO 1
<211> LENGTH: 480
<212> TYPE: DNA
<213> ORGANISM: Betula verrucosa

<400> SEQUENCE: 1

ggcgtgttta actatgaaac cgaaaccacc agcgtgattc cggcggcgcg tctgtttaaa      60

gcgtttattc tggatggcga taacctgttt ccgaaagtgg cgccgcaggc gattagcagc     120

gtggaaaaca ttgaaggcaa cggcggcccg ggcaccatta agaaaatcag cttcccggaa     180

ggctttccgt tcaaatacgt gaaagatcgt gtggatgaag tggatcatac caacttcaaa     240

tacaactaca gcgtgattga aggcggcccg attggcgata ccctggaaaa aattagcaac     300

gaaattaaaa ttgtggcgac cccggatggc ggcagcattc tgaaaattag caacaaatat     360
```

-continued

```
cataccaaag gcgatcatga agtgaaagcg gaacaggtga aagcgagcaa agaaatgggc    420

gaaaccctgc tgcgtgcggt ggaaagctat ctgctggcgc atagcgatgc gtataactaa    480


<210> SEQ ID NO 2
<211> LENGTH: 480
<212> TYPE: DNA
<213> ORGANISM: Betula verrucosa

<400> SEQUENCE: 2

ggcgtgttta actatgaaac cgaaaccacc agcgtgattc cggcggcgcg tctgtttaaa     60

gcgtttattc tggatggcga taaactgttt ccgaaagtgg cgccgcaggc gattagcagc    120

gtggaaaaca ttgaaggcaa cggcggcccg ggcaccatta agaaaatcag cttcccggaa    180

ggctttccgt tcaaatacgt gaaagatcgt gtggatgaag tggatcatac caacttcaaa    240

tacaactaca gcgtgattga aggcggcccg attggcgata ccctggaaaa aattagcaac    300

aaaattaaaa ttgtggcgac cccggatggc ggcagcattc tgaaaattag caacaaatat    360

cataccaaag gcgatcatga agtgaaagcg gaacaggtga aagcgagcaa agaaatgggc    420

gaaaccctgc tgcgtgcggt ggaaagctat ctgctggcgc atagcgatgc gtataactaa    480


<210> SEQ ID NO 3
<211> LENGTH: 159
<212> TYPE: PRT
<213> ORGANISM: Betula verrucosa
<220> FEATURE:
<221> NAME/KEY: 1epitope
<222> LOCATION: (2)..(6)
<220> FEATURE:
<221> NAME/KEY: 1epitope
<222> LOCATION: (70)..(75)
<220> FEATURE:
<221> NAME/KEY: 1epitope
<222> LOCATION: (78)..(84)
<220> FEATURE:
<221> NAME/KEY: 1epitope
<222> LOCATION: (96)..(103)
<220> FEATURE:
<221> NAME/KEY: 1epitope
<222> LOCATION: (115)..(121)

<400> SEQUENCE: 3

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
```

145 150 155

<210> SEQ ID NO 4
<211> LENGTH: 159
<212> TYPE: PRT
<213> ORGANISM: Betula verrucosa

<400> SEQUENCE: 4

```
Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155
```

<210> SEQ ID NO 5
<211> LENGTH: 159
<212> TYPE: PRT
<213> ORGANISM: Betula verrucosa

<400> SEQUENCE: 5

```
Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155
```

```
<210> SEQ ID NO 6
<211> LENGTH: 159
<212> TYPE: PRT
<213> ORGANISM: Betula verrucosa

<400> SEQUENCE: 6

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Val Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 7
<211> LENGTH: 159
<212> TYPE: PRT
<213> ORGANISM: Betula verrucosa

<400> SEQUENCE: 7

Gly Val Phe Asn Tyr Glu Thr Glu Ala Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 8
<211> LENGTH: 159
<212> TYPE: PRT
```

<213> ORGANISM: Betula verrucosa

<400> SEQUENCE: 8

```
Gly Val Phe Asn Tyr Glu Thr Glu Ala Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155
```

<210> SEQ ID NO 9
<211> LENGTH: 159
<212> TYPE: PRT
<213> ORGANISM: Betula verrucosa

<400> SEQUENCE: 9

```
Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Leu Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155
```

<210> SEQ ID NO 10
<211> LENGTH: 159
<212> TYPE: PRT
<213> ORGANISM: Betula verrucosa

<400> SEQUENCE: 10

```
Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Arg Glu Thr Leu Leu
    130                 135                 140

Arg Ala Val Glu Ser Tyr Leu Leu Ala His Ser Asp Ala Tyr Asn
145                 150                 155


<210> SEQ ID NO 11
<211> LENGTH: 159
<212> TYPE: PRT
<213> ORGANISM: Betula verrucosa

<400> SEQUENCE: 11

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Val Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Met Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 12
<211> LENGTH: 159
<212> TYPE: PRT
<213> ORGANISM: Betula verrucosa

<400> SEQUENCE: 12

Gly Val Phe Asn Tyr Glu Thr Glu Thr Thr Ser Val Ile Pro Ala Ala
1               5                   10                  15
```

Arg Leu Phe Lys Ala Phe Phe Leu Asp Gly Asp Asn Leu Phe Pro Lys
20 25 30

Val Ala Pro Gln Ala Ile Ser Ser Val Glu Asn Ile Glu Gly Asn Gly
35 40 45

Gly Pro Gly Thr Ile Lys Lys Ile Ser Phe Pro Glu Gly Phe Pro Phe
50 55 60

Arg Tyr Val Lys Asp Arg Val Asp Glu Val Asp His Thr Asn Phe Lys
65 70 75 80

Tyr Ser Tyr Ser Val Ile Glu Gly Gly Pro Val Gly Asp Thr Leu Glu
85 90 95

Lys Ile Ser Asn Glu Ile Lys Ile Val Ala Thr Pro Asp Gly Gly Ser
100 105 110

Ile Leu Lys Ile Ser Asn Lys Tyr His Thr Lys Gly Asp His Glu Val
115 120 125

Lys Glu Glu Gln Ile Lys Ala Ser Lys Glu Met Gly Glu Thr Leu Leu
130 135 140

Arg Ala Val Glu Ser Tyr Leu Leu Ala His Ser Asp Ala Tyr Asn
145 150 155

<210> SEQ ID NO 13
<211> LENGTH: 159
<212> TYPE: PRT
<213> ORGANISM: Betula verrucosa

<400> SEQUENCE: 13

Gly Val Phe Asn Tyr Glu Thr Glu Ala Thr Ser Val Ile Pro Ala Ala
1 5 10 15

Arg Leu Phe Lys Ala Phe Ile Leu Asp Gly Asp Asn Leu Phe Pro Lys
20 25 30

Val Ala Pro Gln Ala Ile Ser Ser Val Glu Asn Ile Glu Gly Asn Gly
35 40 45

Gly Pro Gly Thr Ile Lys Lys Ile Ser Phe Pro Glu Gly Ile Pro Phe
50 55 60

Lys Tyr Val Lys Gly Arg Val Asp Glu Val Asp His Thr Asn Phe Lys
65 70 75 80

Tyr Ser Tyr Ser Val Ile Glu Gly Gly Pro Val Gly Asp Thr Leu Glu
85 90 95

Lys Ile Ser Asn Glu Ile Lys Ile Val Ala Thr Pro Asn Gly Gly Ser
100 105 110

Ile Leu Lys Ile Asn Asn Lys Tyr His Thr Lys Gly Asp His Glu Val
115 120 125

Lys Ala Glu Gln Ile Lys Ala Ser Lys Glu Met Gly Glu Thr Leu Leu
130 135 140

Arg Ala Val Glu Ser Tyr Leu Leu Ala His Ser Asp Ala Tyr Asn
145 150 155

<210> SEQ ID NO 14
<211> LENGTH: 159
<212> TYPE: PRT
<213> ORGANISM: Betula verrucosa

<400> SEQUENCE: 14

Gly Val Phe Asn Tyr Glu Ile Glu Ala Thr Ser Val Ile Pro Ala Ala
1 5 10 15

Arg Leu Phe Lys Ala Phe Ile Leu Asp Gly Asp Asn Leu Phe Pro Lys
20 25 30

Val Ala Pro Gln Ala Ile Ser Ser Val Glu Asn Ile Glu Gly Asn Gly
35 40 45

Gly Pro Gly Thr Ile Lys Lys Ile Ser Phe Pro Glu Gly Phe Pro Phe
50 55 60

Lys Tyr Val Lys Asp Arg Val Asp Glu Val Asp His Thr Asn Phe Lys
65 70 75 80

Tyr Ser Tyr Ser Val Ile Glu Gly Gly Pro Val Gly Asp Thr Leu Glu
85 90 95

Lys Ile Ser Asn Glu Ile Lys Ile Val Ala Thr Pro Asn Gly Gly Ser
100 105 110

Ile Leu Lys Ile Asn Asn Lys Tyr His Thr Lys Gly Asp His Glu Val
115 120 125

Lys Ala Glu Gln Ile Lys Ala Ser Lys Glu Met Gly Glu Thr Leu Leu
130 135 140

Arg Ala Val Glu Ser Tyr Leu Leu Ala His Ser Asp Ala Tyr Asn
145 150 155

<210> SEQ ID NO 15
<211> LENGTH: 159
<212> TYPE: PRT
<213> ORGANISM: Betula verrucosa

<400> SEQUENCE: 15

Gly Val Phe Asn Tyr Glu Ile Glu Ala Thr Ser Val Ile Pro Ala Ala
1 5 10 15

Arg Leu Phe Lys Ala Phe Ile Leu Asp Gly Asp Asn Leu Phe Pro Lys
20 25 30

Val Ala Pro Gln Ala Ile Ser Ser Val Glu Asn Ile Glu Gly Asn Gly
35 40 45

Gly Pro Gly Thr Ile Lys Lys Ile Ser Phe Pro Glu Gly Phe Pro Phe
50 55 60

Lys Tyr Val Lys Asp Arg Val Asp Glu Val Asp His Thr Asn Phe Lys
65 70 75 80

Tyr Ser Tyr Ser Val Ile Glu Gly Gly Pro Val Gly Asp Thr Leu Glu
85 90 95

Lys Ile Ser Asn Glu Ile Lys Ile Val Ala Thr Pro Asn Gly Gly Ser
100 105 110

Ile Leu Lys Ile Asn Asn Lys Tyr His Thr Lys Gly Asp His Glu Val
115 120 125

Lys Ala Glu Gln Ile Lys Ala Ser Lys Glu Met Gly Glu Thr Leu Leu
130 135 140

Arg Ala Val Glu Ser Tyr Leu Leu Ala His Ser Asp Ala Tyr Asn
145 150 155

<210> SEQ ID NO 16
<211> LENGTH: 159
<212> TYPE: PRT
<213> ORGANISM: Betula verrucosa

<400> SEQUENCE: 16

Gly Val Phe Asn Tyr Glu Thr Glu Ala Thr Ser Val Ile Pro Ala Ala
1 5 10 15

Arg Leu Phe Lys Ala Phe Ile Leu Asp Gly Asp Asn Leu Phe Pro Lys
20 25 30

Val Ala Pro Gln Ala Ile Ser Ser Val Glu Asn Ile Glu Gly Asn Gly
35 40 45

```
Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Ser Tyr Ser Val Ile Glu Gly Gly Pro Val Gly Asp Thr Leu Glu
                85                  90                  95

Lys Ile Ser Asn Glu Ile Lys Ile Val Ala Thr Pro Asn Gly Gly Ser
            100                 105                 110

Ile Leu Lys Ile Asn Asn Lys Tyr His Thr Lys Gly Asp His Glu Val
        115                 120                 125

Lys Ala Glu Gln Ile Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 17
<211> LENGTH: 159
<212> TYPE: PRT
<213> ORGANISM: Betula verrucosa

<400> SEQUENCE: 17

Gly Val Phe Asn Tyr Glu Thr Glu Ala Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Ile Pro Phe
    50                  55                  60

Lys Tyr Val Lys Asp Arg Val Asp Glu Val Asp His Ala Asn Phe Lys
65                  70                  75                  80

Tyr Ser Tyr Ser Val Ile Glu Gly Gly Pro Val Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Ile Lys Ala Ser Lys Glu Met Gly Glu Thr Leu Leu
    130                 135                 140

Arg Ala Val Glu Arg Tyr Leu Leu Ala His Ser Asp Ala Tyr Asn
145                 150                 155


<210> SEQ ID NO 18
<211> LENGTH: 159
<212> TYPE: PRT
<213> ORGANISM: Betula verrucosa

<400> SEQUENCE: 18

Gly Val Phe Asn Tyr Glu Ile Glu Thr Thr Ser Val Ile Pro Ala Ala
1               5                   10                  15

Arg Leu Phe Lys Ala Phe Ile Leu Asp Gly Asp Asn Leu Val Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Asn Phe Pro Glu Gly Phe Pro Phe
    50                  55                  60
```

```
Lys Tyr Val Lys Asp Arg Val Asp Glu Val Asp His Thr Asn Phe Lys
65                  70                  75                  80

Tyr Asn Tyr Ser Val Ile Glu Gly Gly Pro Val Gly Asp Thr Leu Glu
                85                  90                  95

Lys Ile Ser Asn Glu Ile Lys Ile Val Ala Thr Pro Asp Gly Gly Cys
            100                 105                 110

Val Leu Lys Ile Ser Asn Lys Tyr His Thr Lys Gly Asn His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 19
<211> LENGTH: 159
<212> TYPE: PRT
<213> ORGANISM: Betula verrucosa

<400> SEQUENCE: 19

Gly Val Phe Asn Tyr Glu Ile Glu Thr Thr Ser Val Ile Pro Ala Ala
1               5                   10                  15

Arg Leu Phe Lys Ala Phe Ile Leu Asp Gly Asp Asn Leu Val Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Asn Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Val Gly Asp Thr Leu Glu
                85                  90                  95

Lys Ile Ser Asn Glu Ile Lys Ile Val Ala Thr Pro Asp Gly Gly Cys
            100                 105                 110

Val Leu Lys Ile Ser Asn Lys Tyr His Thr Lys Gly Asn His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 20
<211> LENGTH: 159
<212> TYPE: PRT
<213> ORGANISM: Betula verrucosa

<400> SEQUENCE: 20

Gly Val Phe Asn Tyr Glu Ser Glu Thr Thr Ser Val Ile Pro Ala Ala
1               5                   10                  15

Arg Leu Phe Lys Ala Phe Ile Leu Glu Gly Asp Asn Leu Ile Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Asn Phe Pro Glu Gly Phe Pro Phe
    50                  55                  60

Lys Tyr Val Lys Asp Arg Val Asp Glu Val Asp His Thr Asn Phe Lys
65                  70                  75                  80
```

```
Tyr Asn Tyr Ser Val Ile Glu Gly Gly Pro Val Gly Asp Thr Leu Glu
                85                  90                  95

Lys Ile Ser Asn Glu Ile Lys Ile Val Ala Thr Pro Asp Gly Gly Cys
            100                 105                 110

Val Leu Lys Ile Ser Asn Lys Tyr His Thr Lys Gly Asn His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 21
<211> LENGTH: 159
<212> TYPE: PRT
<213> ORGANISM: Betula verrucosa

<400> SEQUENCE: 21

Gly Val Phe Asn Tyr Glu Thr Glu Ala Thr Ser Val Ile Pro Ala Ala
1               5                   10                  15

Arg Met Phe Lys Ala Phe Ile Leu Asp Gly Asp Lys Leu Val Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Asn Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Val Gly Asp Thr Leu Glu
                85                  90                  95

Lys Ile Ser Asn Glu Ile Lys Ile Val Ala Thr Pro Asp Gly Gly Cys
            100                 105                 110

Val Leu Lys Ile Ser Asn Lys Tyr His Thr Lys Gly Asn His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 22
<211> LENGTH: 159
<212> TYPE: PRT
<213> ORGANISM: Betula verrucosa

<400> SEQUENCE: 22

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Val Gly Asp Thr Leu Glu
                85                  90                  95
```

```
Lys Ile Ser Asn Glu Ile Lys Ile Val Ala Thr Pro Asp Gly Gly Cys
            100                 105                 110

Val Leu Lys Ile Ser Asn Lys Tyr His Thr Lys Gly Asn His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 23
<211> LENGTH: 159
<212> TYPE: PRT
<213> ORGANISM: Betula verrucosa

<400> SEQUENCE: 23

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Ile Leu Glu
                85                  90                  95

Lys Ile Ser Asn Glu Ile Lys Ile Val Ala Thr Pro Asp Gly Gly Cys
            100                 105                 110

Val Leu Lys Ile Ser Asn Lys Tyr His Thr Lys Gly Asn His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 24
<211> LENGTH: 159
<212> TYPE: PRT
<213> ORGANISM: Betula verrucosa

<400> SEQUENCE: 24

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Gly Gly Leu Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Cys
            100                 105                 110
```

```
Val Leu Lys Ile Ser Asn Lys Tyr His Thr Lys Gly Asn His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 25
<211> LENGTH: 159
<212> TYPE: PRT
<213> ORGANISM: Betula verrucosa

<400> SEQUENCE: 25

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Ala His Lys Asn Phe Lys
65                  70                  75                  80

Tyr Ser Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Arg Ser
            100                 105                 110

Ile Leu Lys Ile Ser Asn Lys Tyr His Thr Lys Gly Asp His Glu Val
        115                 120                 125

Lys Ala Glu Gln Ile Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155


<210> SEQ ID NO 26
<211> LENGTH: 159
<212> TYPE: PRT
<213> ORGANISM: Betula verrucosa

<400> SEQUENCE: 26

Gly Val Phe Asn Tyr Glu Thr Glu Thr Thr Ser Val Ile Pro Ala Ala
1               5                   10                  15

Arg Leu Phe Lys Ala Phe Ile Leu Glu Gly Asp Thr Leu Ile Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Thr Phe Pro Glu Gly Ser Pro Phe
    50                  55                  60

Lys Tyr Val Lys Glu Arg Val Asp Glu Val Asp His Ala Asn Phe Lys
65                  70                  75                  80

Tyr Ser Tyr Ser Met Ile Glu Gly Gly Ala Leu Gly Asp Thr Leu Glu
                85                  90                  95

Lys Ile Cys Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Met
        115                 120                 125
```

```
Lys Ala Glu His Met Lys Ala Ile Lys Glu Lys Gly Glu Ala Leu Leu
    130                 135                 140

Arg Ala Val Glu Ser Tyr Leu Leu Ala His Ser Asp Ala Tyr Asn
145                 150                 155


<210> SEQ ID NO 27
<211> LENGTH: 159
<212> TYPE: PRT
<213> ORGANISM: Betula verrucosa

<400> SEQUENCE: 27

Gly Val Phe Asn Tyr Glu Ser Glu Thr Thr Ser Val Ile Pro Ala Ala
1               5                   10                  15

Arg Leu Phe Lys Ala Phe Ile Leu Glu Gly Asp Thr Leu Ile Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Thr Phe Pro Glu Gly Ser Pro Phe
    50                  55                  60

Lys Tyr Val Lys Glu Arg Val Asp Glu Val Asp His Ala Asn Phe Lys
65                  70                  75                  80

Tyr Ser Tyr Ser Met Ile Glu Gly Gly Ala Leu Gly Asp Thr Leu Glu
                85                  90                  95

Lys Ile Cys Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Met
        115                 120                 125

Lys Ala Glu His Met Lys Ala Ile Lys Glu Lys Gly Glu Ala Leu Leu
    130                 135                 140

Arg Ala Val Glu Ser Tyr Leu Leu Ala His Ser Asp Ala Tyr Asn
145                 150                 155


<210> SEQ ID NO 28
<211> LENGTH: 159
<212> TYPE: PRT
<213> ORGANISM: Betula verrucosa

<400> SEQUENCE: 28

Gly Val Phe Asn Tyr Glu Ser Glu Thr Thr Ser Val Ile Pro Ala Ala
1               5                   10                  15

Arg Leu Phe Lys Ala Phe Ile Leu Glu Gly Asp Thr Leu Ile Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Thr Phe Pro Glu Gly Ser Pro Phe
    50                  55                  60

Lys Tyr Val Lys Glu Arg Val Asp Glu Val Asp His Ala Asn Phe Lys
65                  70                  75                  80

Tyr Ser Tyr Ser Met Ile Glu Gly Gly Ala Leu Gly Asp Thr Leu Glu
                85                  90                  95

Lys Ile Cys Asn Glu Ile Lys Ile Val Ala Thr Pro Asp Gly Gly Ser
            100                 105                 110

Ile Leu Lys Ile Ser Asn Lys Tyr His Thr Lys Gly Asp Gln Glu Met
        115                 120                 125

Lys Ala Glu His Met Lys Ala Ile Lys Glu Lys Gly Glu Ala Leu Leu
    130                 135                 140
```

Arg Ala Val Glu Ser Tyr Leu Leu Ala His Ser Asp Ala Tyr Asn
145 150 155

<210> SEQ ID NO 29
<211> LENGTH: 159
<212> TYPE: PRT
<213> ORGANISM: Betula verrucosa

<400> SEQUENCE: 29

Gly Val Phe Asn Tyr Glu Ser Glu Thr Thr Ser Val Ile Pro Ala Ala
1 5 10 15

Arg Leu Phe Lys Ala Phe Ile Leu Asp Gly Asp Asn Leu Ile Pro Lys
20 25 30

Val Ala Pro Gln Ala Ile Ser Ser Val Glu Asn Ile Glu Gly Asn Gly
35 40 45

Gly Pro Gly Thr Ile Lys Lys Ile Thr Phe Pro Glu Gly Ser Pro Phe
50 55 60

Lys Tyr Val Lys Glu Arg Val Asp Glu Val Asp His Ala Asn Phe Lys
65 70 75 80

Tyr Ser Tyr Ser Met Ile Glu Gly Gly Ala Leu Gly Asp Thr Leu Glu
85 90 95

Lys Ile Cys Asn Glu Ile Lys Ile Val Ala Thr Pro Asp Gly Gly Ser
100 105 110

Ile Leu Lys Ile Ser Asn Lys Tyr His Thr Lys Gly Asp His Glu Met
115 120 125

Lys Ala Glu His Met Lys Ala Ile Lys Glu Lys Gly Glu Ala Leu Leu
130 135 140

Arg Ala Val Glu Ser Tyr Leu Leu Ala His Ser Asp Ala Tyr Asn
145 150 155

<210> SEQ ID NO 30
<211> LENGTH: 159
<212> TYPE: PRT
<213> ORGANISM: Betula verrucosa

<400> SEQUENCE: 30

Gly Val Phe Asn Tyr Glu Ser Glu Thr Thr Ser Val Ile Pro Ala Ala
1 5 10 15

Arg Leu Phe Lys Ala Phe Ile Leu Asp Gly Asp Asn Leu Ile Pro Lys
20 25 30

Val Ala Pro Gln Ala Ile Ser Ser Val Glu Asn Ile Glu Gly Asn Gly
35 40 45

Gly Pro Gly Thr Ile Lys Lys Ile Thr Phe Pro Glu Gly Ser Pro Phe
50 55 60

Lys Tyr Val Lys Glu Arg Val Asp Glu Val Asp His Ala Asn Phe Lys
65 70 75 80

Tyr Ser Tyr Ser Met Ile Glu Gly Gly Ala Leu Gly Asp Thr Leu Glu
85 90 95

Lys Ile Cys Asn Glu Ile Lys Ile Val Ala Thr Pro Asp Gly Gly Ser
100 105 110

Ile Leu Lys Ile Ser Asn Lys Tyr His Thr Lys Gly Asp His Glu Met
115 120 125

Lys Ala Glu His Met Lys Ala Ile Lys Glu Lys Gly Glu Ala Leu Leu
130 135 140

Arg Ala Val Glu Ser Tyr Leu Leu Ala His Ser Asp Ala Tyr Asn
145 150 155

<210> SEQ ID NO 31
<211> LENGTH: 159
<212> TYPE: PRT
<213> ORGANISM: Betula verrucosa

<400> SEQUENCE: 31

```
Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Ile Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Thr Phe Pro Glu Gly Ser Pro Phe
    50                  55                  60

Lys Tyr Val Lys Glu Arg Val Asp Glu Val Asp His Ala Asn Phe Lys
65                  70                  75                  80

Tyr Ala Tyr Ser Met Ile Glu Gly Gly Ala Leu Gly Asp Thr Leu Glu
                85                  90                  95

Lys Ile Cys Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Met
        115                 120                 125

Lys Ala Glu His Met Lys Ala Ile Lys Glu Lys Gly Glu Ala Leu Leu
    130                 135                 140

Arg Ala Val Glu Ser Tyr Leu Leu Ala His Ser Asp Ala Tyr Asn
145                 150                 155
```

<210> SEQ ID NO 32
<211> LENGTH: 159
<212> TYPE: PRT
<213> ORGANISM: Betula verrucosa

<400> SEQUENCE: 32

```
Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Ile Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Thr Phe Pro Glu Gly Ser Pro Phe
    50                  55                  60

Lys Tyr Val Lys Glu Arg Val Asp Glu Val Asp His Ala Asn Phe Lys
65                  70                  75                  80

Tyr Ser Tyr Ser Met Ile Glu Gly Gly Ala Leu Gly Asp Thr Leu Glu
                85                  90                  95

Lys Ile Cys Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Met
        115                 120                 125

Lys Ala Glu His Met Lys Ala Ile Lys Glu Lys Gly Glu Ala Leu Leu
    130                 135                 140

Arg Ala Val Glu Ser Tyr Leu Leu Ala His Ser Asp Ala Tyr Asn
145                 150                 155
```

<210> SEQ ID NO 33

-continued

```
<211> LENGTH: 159
<212> TYPE: PRT
<213> ORGANISM: Betula verrucosa

<400> SEQUENCE: 33

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Ile Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Thr Phe Pro Glu Gly Ser Pro Phe
    50                  55                  60

Lys Tyr Val Lys Glu Arg Val Asp Glu Val Asp His Ala Asn Phe Lys
65                  70                  75                  80

Tyr Ser Tyr Ser Met Ile Glu Gly Gly Ala Leu Gly Asp Thr Leu Glu
                85                  90                  95

Lys Ile Cys Asn Glu Ile Lys Leu Val Ala Thr Pro Asp Gly Gly Ser
            100                 105                 110

Ile Leu Lys Ile Ser Asn Lys Tyr His Thr Lys Gly Asp His Glu Met
        115                 120                 125

Lys Ala Glu His Met Lys Ala Ile Lys Glu Lys Ala Glu Ala Leu Leu
    130                 135                 140

Arg Ala Val Glu Ser Tyr Leu Leu Ala His Ser Asp Ala Tyr Asn
145                 150                 155


<210> SEQ ID NO 34
<211> LENGTH: 159
<212> TYPE: PRT
<213> ORGANISM: Betula verrucosa

<400> SEQUENCE: 34

Gly Val Phe Asp Tyr Glu Gly Glu Thr Thr Ser Val Ile Pro Ala Ala
1               5                   10                  15

Arg Leu Phe Lys Ala Phe Ile Leu Asp Gly Asp Asn Leu Ile Pro Lys
            20                  25                  30

Val Ala Pro Gln Thr Val Ser Cys Val Glu Asn Ile Glu Gly Asn Gly
        35                  40                  45

Gly Pro Gly Thr Ile Lys Lys Ile Thr Phe Pro Glu Gly Ser Pro Phe
    50                  55                  60

Lys Tyr Val Lys Glu Arg Val Asp Glu Val Asp His Val Asn Phe Lys
65                  70                  75                  80

Tyr Ser Tyr Ser Val Ile Glu Gly Gly Ala Val Gly Asp Thr Leu Glu
                85                  90                  95

Lys Ile Cys Asn Glu Ile Lys Ile Val Pro Ala Pro Gly Gly Gly Ser
            100                 105                 110

Ile Leu Lys Ile Ser Asn Lys Tyr His Thr Lys Gly Asn His Glu Met
        115                 120                 125

Lys Ala Glu Gln Ile Lys Ala Ser Lys Glu Lys Ala Glu Ala Leu Phe
    130                 135                 140

Arg Ala Val Glu Ser Tyr Leu Leu Ala His Ser Asp Ala Tyr Asn
145                 150                 155


<210> SEQ ID NO 35
<211> LENGTH: 159
<212> TYPE: PRT
<213> ORGANISM: Betula verrucosa
```

<400> SEQUENCE: 35

Gly Val Phe Asp Tyr Glu Gly Glu Thr Thr Ser Val Ile Pro Ala Ala
1 5 10 15

Arg Leu Phe Lys Ala Phe Ile Leu Asp Gly Asp Asn Leu Ile Pro Lys
20 25 30

Val Ala Pro Gln Ala Val Ser Cys Val Glu Asn Ile Glu Gly Asn Gly
35 40 45

Gly Pro Gly Thr Ile Lys Lys Ile Thr Phe Pro Glu Gly Ser Pro Phe
50 55 60

Lys Tyr Val Lys Glu Arg Val Asp Glu Val Asp Arg Val Asn Phe Lys
65 70 75 80

Tyr Ser Tyr Ser Val Ile Glu Gly Gly Ala Val Gly Asp Thr Leu Glu
85 90 95

Lys Ile Cys Asn Glu Ile Lys Ile Val Pro Ala Pro Gly Gly Gly Ser
100 105 110

Ile Leu Lys Ile Ser Asn Lys Tyr His Thr Lys Gly Asn His Glu Met
115 120 125

Lys Ala Glu Gln Ile Lys Ala Ser Lys Glu Lys Ala Glu Ala Leu Phe
130 135 140

Arg Ala Val Glu Ser Tyr Leu Leu Ala His Ser Asp Ala Tyr Asn
145 150 155

<210> SEQ ID NO 36
<211> LENGTH: 159
<212> TYPE: PRT
<213> ORGANISM: Betula verrucosa

<400> SEQUENCE: 36

Gly Val Phe Asn Tyr Glu Thr Glu Thr Pro Ser Val Ile Pro Ala Ala
1 5 10 15

Arg Leu Phe Lys Ala Phe Ile Leu Asp Gly Asp Lys Leu Leu Pro Lys
20 25 30

Val Ala Pro Glu Ala Val Ser Ser Val Glu Asn Ile Glu Gly Asn Gly
35 40 45

Gly Pro Gly Thr Ile Lys Lys Ile Thr Phe Pro Glu Gly Ser Pro Phe
50 55 60

Lys Tyr Val Lys Glu Arg Val Asp Glu Val Asp Arg Val Asn Phe Lys
65 70 75 80

Tyr Ser Phe Ser Val Ile Glu Gly Gly Ala Val Gly Asp Ala Leu Glu
85 90 95

Lys Val Cys Asn Glu Ile Lys Ile Val Ala Ala Pro Asp Gly Gly Ser
100 105 110

Ile Leu Lys Ile Ser Asn Lys Phe His Thr Lys Gly Asp His Glu Ile
115 120 125

Asn Ala Glu Gln Ile Lys Ile Glu Lys Glu Lys Ala Glu Gly Leu Leu
130 135 140

Lys Ala Val Glu Ser Tyr His Leu Ala His Ser Asp Ala Tyr Asn
145 150 155

<210> SEQ ID NO 37
<211> LENGTH: 159
<212> TYPE: PRT
<213> ORGANISM: Betula verrucosa

<400> SEQUENCE: 37

```
Gly Val Phe Asn Tyr Glu Thr Glu Ala Thr Ser Val Ile Pro Ala Ala
1               5                   10                  15

Arg Leu Phe Lys Ala Ser Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Ser Pro Phe
    50                  55                  60

Lys Tyr Val Lys Glu Arg Val Asp Glu Val Asp Arg Val Asn Phe Lys
65                  70                  75                  80

Tyr Ser Phe Ser Val Ile Glu Gly Gly Ala Val Gly Asp Ala Leu Glu
                85                  90                  95

Lys Val Cys Asn Glu Ile Lys Ile Val Ala Ala Pro Asp Gly Gly Ser
            100                 105                 110

Ile Leu Lys Ile Ser Asn Lys Phe His Thr Lys Gly Asp His Glu Ile
        115                 120                 125

Asn Ala Glu Gln Ile Lys Ile Glu Lys Glu Lys Ala Val Gly Leu Leu
    130                 135                 140

Lys Ala Val Glu Ser Tyr Leu Leu Ala His Ser Asp Ala Tyr Asn
145                 150                 155


<210> SEQ ID NO 38
<211> LENGTH: 159
<212> TYPE: PRT
<213> ORGANISM: Betula verrucosa

<400> SEQUENCE: 38

Gly Val Phe Asn Tyr Glu Asp Glu Ala Thr Ser Val Ile Ala Pro Ala
1               5                   10                  15

Arg Leu Phe Lys Ser Phe Val Leu Asp Ala Asp Asn Leu Ile Pro Lys
            20                  25                  30

Val Ala Pro Glu Asn Val Ser Ser Ala Glu Asn Ile Glu Gly Asn Gly
        35                  40                  45

Gly Pro Gly Thr Ile Lys Lys Ile Thr Phe Pro Glu Gly Ser His Phe
    50                  55                  60

Lys Tyr Met Lys His Arg Val Asp Glu Ile Asp His Ala Asn Phe Lys
65                  70                  75                  80

Tyr Cys Tyr Ser Ile Ile Glu Gly Gly Pro Leu Gly Asp Thr Leu Glu
                85                  90                  95

Lys Ile Ser Tyr Glu Ile Lys Ile Val Ala Ala Pro Gly Gly Gly Ser
            100                 105                 110

Ile Leu Lys Ile Thr Ser Lys Tyr His Thr Lys Gly Asp Ile Ser Leu
        115                 120                 125

Asn Glu Glu Glu Ile Lys Ala Gly Lys Glu Lys Gly Ala Gly Leu Phe
    130                 135                 140

Lys Ala Val Glu Asn Tyr Leu Val Ala His Pro Asn Ala Tyr Asn
145                 150                 155


<210> SEQ ID NO 39
<211> LENGTH: 159
<212> TYPE: PRT
<213> ORGANISM: Betula verrucosa
<220> FEATURE:
<221> NAME/KEY: MISC_FEATURE
<222> LOCATION: (25)..(25)
<223> OTHER INFORMATION: X is D, K, R, Y, H, or L
<220> FEATURE:
<221> NAME/KEY: MISC_FEATURE
```

<222> LOCATION: (28)..(28)
<223> OTHER INFORMATION: X is N, K, R, Y, I, or W
<220> FEATURE:
<221> NAME/KEY: MISC_FEATURE
<222> LOCATION: (43)..(43)
<223> OTHER INFORMATION: X is N, Y, H, I, L, or E
<220> FEATURE:
<221> NAME/KEY: MISC_FEATURE
<222> LOCATION: (46)..(46)
<223> OTHER INFORMATION: X is G, P, V, D, T, or L
<220> FEATURE:
<221> NAME/KEY: MISC_FEATURE
<222> LOCATION: (47)..(47)
<223> OTHER INFORMATION: X is N, E, L, I, Y, or P
<220> FEATURE:
<221> NAME/KEY: MISC_FEATURE
<222> LOCATION: (80)..(80)
<223> OTHER INFORMATION: X is K, Y, E, W, I, or L
<220> FEATURE:
<221> NAME/KEY: MISC_FEATURE
<222> LOCATION: (82)..(82)
<223> OTHER INFORMATION: X is N, K, R, Y, E, or L
<220> FEATURE:
<221> NAME/KEY: MISC_FEATURE
<222> LOCATION: (84)..(84)
<223> OTHER INFORMATION: X is S, K, R, D, E, or Y
<220> FEATURE:
<221> NAME/KEY: MISC_FEATURE
<222> LOCATION: (99)..(99)
<223> OTHER INFORMATION: X is S, K, R, D, Y, or V
<220> FEATURE:
<221> NAME/KEY: MISC_FEATURE
<222> LOCATION: (101)..(101)
<223> OTHER INFORMATION: X is E, K, R, Y, I, or W
<220> FEATURE:
<221> NAME/KEY: MISC_FEATURE
<222> LOCATION: (117)..(117)
<223> OTHER INFORMATION: X is S, K, R, D, Y, or L
<220> FEATURE:
<221> NAME/KEY: MISC_FEATURE
<222> LOCATION: (119)..(119)
<223> OTHER INFORMATION: X is K, E, Y,  L, W, or I
<220> FEATURE:
<221> NAME/KEY: MISC_FEATURE
<222> LOCATION: (158)..(158)
<223> OTHER INFORMATION: X is Y, D, E, L, P, or I

<400> SEQUENCE: 39

```
Gly Val Phe Asn Tyr Glu Thr Glu Thr Thr Ser Val Ile Pro Ala Ala
1               5                   10                  15

Arg Leu Phe Lys Ala Phe Ile Leu Xaa Gly Asp Xaa Leu Phe Pro Lys
            20                  25                  30

Val Ala Pro Gln Ala Ile Ser Ser Val Glu Xaa Ile Glu Xaa Xaa Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Xaa
65                  70                  75                  80

Tyr Xaa Tyr Xaa Val Ile Glu Gly Gly Pro Ile Gly Asp Thr Leu Glu
                85                  90                  95

Lys Ile Xaa Asn Xaa Ile Lys Ile Val Ala Thr Pro Asp Gly Gly Ser
            100                 105                 110

Ile Leu Lys Ile Xaa Asn Xaa Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Xaa Asn
145                 150                 155
```

<210> SEQ ID NO 40
<211> LENGTH: 159
<212> TYPE: PRT
<213> ORGANISM: Betula verrucosa

<400> SEQUENCE: 40

```
Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Lys Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Lys Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155
```

<210> SEQ ID NO 41
<211> LENGTH: 159
<212> TYPE: PRT
<213> ORGANISM: Betula verrucosa
<220> FEATURE:
<221> NAME/KEY: MISC_FEATURE
<222> LOCATION: (25)..(25)
<223> OTHER INFORMATION: X is D, K, R, Y, H, or L
<220> FEATURE:
<221> NAME/KEY: MISC_FEATURE
<222> LOCATION: (28)..(28)
<223> OTHER INFORMATION: X is N, K, R, Y, I, or W
<220> FEATURE:
<221> NAME/KEY: MISC_FEATURE
<222> LOCATION: (43)..(43)
<223> OTHER INFORMATION: X is N, Y, H, I, L, or E
<220> FEATURE:
<221> NAME/KEY: MISC_FEATURE
<222> LOCATION: (46)..(46)
<223> OTHER INFORMATION: X is G, P, V, D, T, or L
<220> FEATURE:
<221> NAME/KEY: MISC_FEATURE
<222> LOCATION: (47)..(47)
<223> OTHER INFORMATION: X is N, E, L, I, Y, or P
<220> FEATURE:
<221> NAME/KEY: MISC_FEATURE
<222> LOCATION: (80)..(80)
<223> OTHER INFORMATION: X is K, Y, E, W, I, or L
<220> FEATURE:
<221> NAME/KEY: MISC_FEATURE
<222> LOCATION: (82)..(82)
<223> OTHER INFORMATION: X is N, K, R, Y, E, or L
<220> FEATURE:
<221> NAME/KEY: MISC_FEATURE
<222> LOCATION: (84)..(84)
<223> OTHER INFORMATION: X is S, K, R, D, E, or Y
<220> FEATURE:
<221> NAME/KEY: MISC_FEATURE
<222> LOCATION: (99)..(99)
<223> OTHER INFORMATION: X is S, K, R, D, Y, or V

```
<220> FEATURE:
<221> NAME/KEY: MISC_FEATURE
<222> LOCATION: (101)..(101)
<223> OTHER INFORMATION: X is K, R, Y, I or W
<220> FEATURE:
<221> NAME/KEY: MISC_FEATURE
<222> LOCATION: (117)..(117)
<223> OTHER INFORMATION: X is S, K, R, D, Y or L
<220> FEATURE:
<221> NAME/KEY: MISC_FEATURE
<222> LOCATION: (119)..(119)
<223> OTHER INFORMATION: X is K, E, Y, L, W, or I
<220> FEATURE:
<221> NAME/KEY: MISC_FEATURE
<222> LOCATION: (158)..(158)
<223> OTHER INFORMATION: X is Y, D, E, L, P, or I

<400> SEQUENCE: 41

Gly Val Phe Asn Tyr Glu Thr Glu Thr Thr Ser Val Ile Pro Ala Ala
1               5                   10                  15

Arg Leu Phe Lys Ala Phe Ile Leu Xaa Gly Asp Xaa Leu Phe Pro Lys
            20                  25                  30

Val Ala Pro Gln Ala Ile Ser Ser Val Glu Xaa Ile Glu Xaa Xaa Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Xaa
65                  70                  75                  80

Tyr Xaa Tyr Xaa Val Ile Glu Gly Gly Pro Ile Gly Asp Thr Leu Glu
                85                  90                  95

Lys Ile Xaa Asn Xaa Ile Lys Ile Val Ala Thr Pro Asp Gly Gly Ser
            100                 105                 110

Ile Leu Lys Ile Xaa Asn Xaa Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Xaa Asn
145                 150                 155


<210> SEQ ID NO 42
<211> LENGTH: 159
<212> TYPE: PRT
<213> ORGANISM: Betula verrucosa
<220> FEATURE:
<221> NAME/KEY: MISC_FEATURE
<222> LOCATION: (25)..(25)
<223> OTHER INFORMATION: X is D, K, R, Y, H, or L
<220> FEATURE:
<221> NAME/KEY: MISC_FEATURE
<222> LOCATION: (28)..(28)
<223> OTHER INFORMATION: X is N, K, R, Y, I, or W
<220> FEATURE:
<221> NAME/KEY: MISC_FEATURE
<222> LOCATION: (43)..(43)
<223> OTHER INFORMATION: X is N, Y, H, I, L, or E
<220> FEATURE:
<221> NAME/KEY: MISC_FEATURE
<222> LOCATION: (46)..(46)
<223> OTHER INFORMATION: X is G, P, V, D, T, or L
<220> FEATURE:
<221> NAME/KEY: MISC_FEATURE
<222> LOCATION: (47)..(47)
<223> OTHER INFORMATION: X is N, E, L, I, Y, or P
<220> FEATURE:
<221> NAME/KEY: MISC_FEATURE
<222> LOCATION: (80)..(80)
<223> OTHER INFORMATION: X is Y, E, W, I, or L
<220> FEATURE:
```

<221> NAME/KEY: MISC_FEATURE
<222> LOCATION: (82)..(82)
<223> OTHER INFORMATION: X is N, K, R, Y, E, or L
<220> FEATURE:
<221> NAME/KEY: MISC_FEATURE
<222> LOCATION: (84)..(84)
<223> OTHER INFORMATION: X is S, K, R, D, E, or Y
<220> FEATURE:
<221> NAME/KEY: MISC_FEATURE
<222> LOCATION: (99)..(99)
<223> OTHER INFORMATION: X is S, K, R, D, Y, or V
<220> FEATURE:
<221> NAME/KEY: MISC_FEATURE
<222> LOCATION: (101)..(101)
<223> OTHER INFORMATION: X is E, K, R, Y, I, or W
<220> FEATURE:
<221> NAME/KEY: MISC_FEATURE
<222> LOCATION: (117)..(117)
<223> OTHER INFORMATION: X is S, K, R, D, Y, or L
<220> FEATURE:
<221> NAME/KEY: MISC_FEATURE
<222> LOCATION: (119)..(119)
<223> OTHER INFORMATION: X is K, E, Y,  L, W, or I
<220> FEATURE:
<221> NAME/KEY: MISC_FEATURE
<222> LOCATION: (158)..(158)
<223> OTHER INFORMATION: X is Y, D, E, L, P, or I

<400> SEQUENCE: 42

```
Gly Val Phe Asn Tyr Glu Thr Glu Thr Thr Ser Val Ile Pro Ala Ala
1               5                   10                  15

Arg Leu Phe Lys Ala Phe Ile Leu Xaa Gly Asp Xaa Leu Phe Pro Lys
            20                  25                  30

Val Ala Pro Gln Ala Ile Ser Ser Val Glu Xaa Ile Glu Xaa Xaa Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Xaa
65                  70                  75                  80

Tyr Xaa Tyr Xaa Val Ile Glu Gly Gly Pro Ile Gly Asp Thr Leu Glu
                85                  90                  95

Lys Ile Xaa Asn Xaa Ile Lys Ile Val Ala Thr Pro Asp Gly Gly Ser
            100                 105                 110

Ile Leu Lys Ile Xaa Asn Xaa Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Xaa Asn
145                 150                 155
```

<210> SEQ ID NO 43
<211> LENGTH: 159
<212> TYPE: PRT
<213> ORGANISM: Betula verrucosa
<220> FEATURE:
<221> NAME/KEY: MISC_FEATURE
<222> LOCATION: (25)..(25)
<223> OTHER INFORMATION: X is D, K, R, Y, H, or L
<220> FEATURE:
<221> NAME/KEY: MISC_FEATURE
<222> LOCATION: (28)..(28)
<223> OTHER INFORMATION: X is N, K, R, Y, I, or W
<220> FEATURE:
<221> NAME/KEY: MISC_FEATURE
<222> LOCATION: (43)..(43)
<223> OTHER INFORMATION: X is N, Y, H, I, L, or E
<220> FEATURE:
<221> NAME/KEY: MISC_FEATURE
<222> LOCATION: (46)..(46)
<223> OTHER INFORMATION: X is G, P, V, D, T, or L
<220> FEATURE:
<221> NAME/KEY: MISC_FEATURE
<222> LOCATION: (47)..(47)
<223> OTHER INFORMATION: X is N, E, L, I, Y, or P
<220> FEATURE:
<221> NAME/KEY: MISC_FEATURE
<222> LOCATION: (80)..(80)
<223> OTHER INFORMATION: X is K, Y, E, W, I, or L
<220> FEATURE:
<221> NAME/KEY: MISC_FEATURE
<222> LOCATION: (82)..(82)
<223> OTHER INFORMATION: X is K, R, Y, E, or L
<220> FEATURE:
<221> NAME/KEY: MISC_FEATURE
<222> LOCATION: (84)..(84)
<223> OTHER INFORMATION: X is S, K, R, D, E, or Y
<220> FEATURE:
<221> NAME/KEY: MISC_FEATURE
<222> LOCATION: (99)..(99)
<223> OTHER INFORMATION: X is S, K, R, D, Y, or V
<220> FEATURE:
<221> NAME/KEY: MISC_FEATURE
<222> LOCATION: (101)..(101)
<223> OTHER INFORMATION: X is E, K, R, Y, I, or W
<220> FEATURE:
<221> NAME/KEY: MISC_FEATURE
<222> LOCATION: (117)..(117)
<223> OTHER INFORMATION: X is S, K, R, D, Y, or L
<220> FEATURE:
<221> NAME/KEY: MISC_FEATURE
<222> LOCATION: (119)..(119)
<223> OTHER INFORMATION: X is K, E, Y, L, W, or I
<220> FEATURE:
<221> NAME/KEY: MISC_FEATURE
<222> LOCATION: (158)..(158)
<223> OTHER INFORMATION: X is Y, D, E, L, P, or I

<400> SEQUENCE: 43

```
Gly Val Phe Asn Tyr Glu Thr Glu Thr Thr Ser Val Ile Pro Ala Ala
1               5                   10                  15

Arg Leu Phe Lys Ala Phe Ile Leu Xaa Gly Asp Xaa Leu Phe Pro Lys
            20                  25                  30

Val Ala Pro Gln Ala Ile Ser Ser Val Glu Xaa Ile Glu Xaa Xaa Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Xaa
65                  70                  75                  80

Tyr Xaa Tyr Xaa Val Ile Glu Gly Gly Pro Ile Gly Asp Thr Leu Glu
                85                  90                  95

Lys Ile Xaa Asn Xaa Ile Lys Ile Val Ala Thr Pro Asp Gly Gly Ser
            100                 105                 110

Ile Leu Lys Ile Xaa Asn Xaa Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Xaa Asn
145                 150                 155
```

<210> SEQ ID NO 44
<211> LENGTH: 159
<212> TYPE: PRT
<213> ORGANISM: Betula verrucosa
<220> FEATURE:
<221> NAME/KEY: MISC_FEATURE
<222> LOCATION: (25)..(25)

```
<223> OTHER INFORMATION: X is D, K, R, Y, H, or L
<220> FEATURE:
<221> NAME/KEY: MISC_FEATURE
<222> LOCATION: (28)..(28)
<223> OTHER INFORMATION: X is N, K, R, Y, I, or W
<220> FEATURE:
<221> NAME/KEY: MISC_FEATURE
<222> LOCATION: (43)..(43)
<223> OTHER INFORMATION: X is N, Y, H, I, L, or E
<220> FEATURE:
<221> NAME/KEY: MISC_FEATURE
<222> LOCATION: (46)..(46)
<223> OTHER INFORMATION: X is G, P, V, D, T, or L
<220> FEATURE:
<221> NAME/KEY: MISC_FEATURE
<222> LOCATION: (47)..(47)
<223> OTHER INFORMATION: X is N, E, L, I, Y, or P
<220> FEATURE:
<221> NAME/KEY: MISC_FEATURE
<222> LOCATION: (80)..(80)
<223> OTHER INFORMATION: X is K, Y, E, W, I, or L
<220> FEATURE:
<221> NAME/KEY: MISC_FEATURE
<222> LOCATION: (82)..(82)
<223> OTHER INFORMATION: X is N, K, R, Y, E, or L
<220> FEATURE:
<221> NAME/KEY: MISC_FEATURE
<222> LOCATION: (84)..(84)
<223> OTHER INFORMATION: X is K, R, D, E, or Y
<220> FEATURE:
<221> NAME/KEY: MISC_FEATURE
<222> LOCATION: (99)..(99)
<223> OTHER INFORMATION: X is S, K, R, D, Y, or V
<220> FEATURE:
<221> NAME/KEY: MISC_FEATURE
<222> LOCATION: (101)..(101)
<223> OTHER INFORMATION: X is E, K, R, Y, I, or W
<220> FEATURE:
<221> NAME/KEY: MISC_FEATURE
<222> LOCATION: (117)..(117)
<223> OTHER INFORMATION: X is S, K, R, D, Y, or L
<220> FEATURE:
<221> NAME/KEY: MISC_FEATURE
<222> LOCATION: (119)..(119)
<223> OTHER INFORMATION: X is K, E, Y,  L, W, or I
<220> FEATURE:
<221> NAME/KEY: MISC_FEATURE
<222> LOCATION: (158)..(158)
<223> OTHER INFORMATION: X is Y, D, E, L, P, or I

<400> SEQUENCE: 44

Gly Val Phe Asn Tyr Glu Thr Glu Thr Thr Ser Val Ile Pro Ala Ala
1               5                   10                  15

Arg Leu Phe Lys Ala Phe Ile Leu Xaa Gly Asp Xaa Leu Phe Pro Lys
            20                  25                  30

Val Ala Pro Gln Ala Ile Ser Ser Val Glu Xaa Ile Glu Xaa Xaa Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Xaa
65                  70                  75                  80

Tyr Xaa Tyr Xaa Val Ile Glu Gly Gly Pro Ile Gly Asp Thr Leu Glu
                85                  90                  95

Lys Ile Xaa Asn Xaa Ile Lys Ile Val Ala Thr Pro Asp Gly Gly Ser
            100                 105                 110

Ile Leu Lys Ile Xaa Asn Xaa Tyr His Thr Lys Gly Asp His Glu Val
        115                 120                 125

Lys Ala Glu Gln Val Lys Ala Ser Lys Glu Met Gly Glu Thr Leu Leu
    130                 135                 140
```

Arg Ala Val Glu Ser Tyr Leu Leu Ala His Ser Asp Ala Xaa Asn
145 150 155

<210> SEQ ID NO 45
<211> LENGTH: 159
<212> TYPE: PRT
<213> ORGANISM: Betula verrucosa
<220> FEATURE:
<221> NAME/KEY: MISC_FEATURE
<222> LOCATION: (25)..(25)
<223> OTHER INFORMATION: X is D, K, R, Y, H, or L
<220> FEATURE:
<221> NAME/KEY: MISC_FEATURE
<222> LOCATION: (28)..(28)
<223> OTHER INFORMATION: X is N, K, R, Y, I, or W
<220> FEATURE:
<221> NAME/KEY: MISC_FEATURE
<222> LOCATION: (43)..(43)
<223> OTHER INFORMATION: X is N, Y, H, I, L, or E
<220> FEATURE:
<221> NAME/KEY: MISC_FEATURE
<222> LOCATION: (46)..(46)
<223> OTHER INFORMATION: X is G, P, V, D, T, or L
<220> FEATURE:
<221> NAME/KEY: MISC_FEATURE
<222> LOCATION: (47)..(47)
<223> OTHER INFORMATION: X is N, E, L, I, Y, or P
<220> FEATURE:
<221> NAME/KEY: MISC_FEATURE
<222> LOCATION: (80)..(80)
<223> OTHER INFORMATION: X is K, Y, E, W, I, or L
<220> FEATURE:
<221> NAME/KEY: MISC_FEATURE
<222> LOCATION: (82)..(82)
<223> OTHER INFORMATION: X is N, K, R, Y, E, or L
<220> FEATURE:
<221> NAME/KEY: MISC_FEATURE
<222> LOCATION: (84)..(84)
<223> OTHER INFORMATION: X is S, K, R, D, E, or Y
<220> FEATURE:
<221> NAME/KEY: MISC_FEATURE
<222> LOCATION: (99)..(99)
<223> OTHER INFORMATION: X is K, R, D, Y, or V
<220> FEATURE:
<221> NAME/KEY: MISC_FEATURE
<222> LOCATION: (101)..(101)
<223> OTHER INFORMATION: X is E, K, R, Y, I, or W
<220> FEATURE:
<221> NAME/KEY: MISC_FEATURE
<222> LOCATION: (117)..(117)
<223> OTHER INFORMATION: X is S, K, R, D, Y, or L
<220> FEATURE:
<221> NAME/KEY: MISC_FEATURE
<222> LOCATION: (119)..(119)
<223> OTHER INFORMATION: X is K, E, Y, L, W, or I
<220> FEATURE:
<221> NAME/KEY: MISC_FEATURE
<222> LOCATION: (158)..(158)
<223> OTHER INFORMATION: X is Y, D, E, L, P, or I

<400> SEQUENCE: 45

Gly Val Phe Asn Tyr Glu Thr Glu Thr Thr Ser Val Ile Pro Ala Ala
1 5 10 15

Arg Leu Phe Lys Ala Phe Ile Leu Xaa Gly Asp Xaa Leu Phe Pro Lys
20 25 30

Val Ala Pro Gln Ala Ile Ser Ser Val Glu Xaa Ile Glu Xaa Xaa Gly
35 40 45

Gly Pro Gly Thr Ile Lys Lys Ile Ser Phe Pro Glu Gly Phe Pro Phe
50 55 60

Lys Tyr Val Lys Asp Arg Val Asp Glu Val Asp His Thr Asn Phe Xaa
65 70 75 80

Tyr Xaa Tyr Xaa Val Ile Glu Gly Gly Pro Ile Gly Asp Thr Leu Glu

```
                85                  90                  95

Lys Ile Xaa Asn Xaa Ile Lys Ile Val Ala Thr Pro Asp Gly Gly Ser
            100                 105                 110

Ile Leu Lys Ile Xaa Asn Xaa Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Xaa Asn
145                 150                 155


<210> SEQ ID NO 46
<211> LENGTH: 159
<212> TYPE: PRT
<213> ORGANISM: Betula verrucosa
<220> FEATURE:
<221> NAME/KEY: MISC_FEATURE
<222> LOCATION: (25)..(25)
<223> OTHER INFORMATION: X is D, K, R, Y, H, or L
<220> FEATURE:
<221> NAME/KEY: MISC_FEATURE
<222> LOCATION: (28)..(28)
<223> OTHER INFORMATION: X is N, K, R, Y, I, or W
<220> FEATURE:
<221> NAME/KEY: MISC_FEATURE
<222> LOCATION: (43)..(43)
<223> OTHER INFORMATION: X is N, Y, H, I, L, or E
<220> FEATURE:
<221> NAME/KEY: MISC_FEATURE
<222> LOCATION: (46)..(46)
<223> OTHER INFORMATION: X is G, P, V, D, T, or L
<220> FEATURE:
<221> NAME/KEY: MISC_FEATURE
<222> LOCATION: (47)..(47)
<223> OTHER INFORMATION: X is N, E, L, I, Y, or P
<220> FEATURE:
<221> NAME/KEY: MISC_FEATURE
<222> LOCATION: (80)..(80)
<223> OTHER INFORMATION: X is K, Y, E, W, I, or L
<220> FEATURE:
<221> NAME/KEY: MISC_FEATURE
<222> LOCATION: (82)..(82)
<223> OTHER INFORMATION: X is N, K, R, Y, E, or L
<220> FEATURE:
<221> NAME/KEY: MISC_FEATURE
<222> LOCATION: (84)..(84)
<223> OTHER INFORMATION: X is S, K, R, D, E, or Y
<220> FEATURE:
<221> NAME/KEY: MISC_FEATURE
<222> LOCATION: (99)..(99)
<223> OTHER INFORMATION: X is S, K, R, D, Y, or V
<220> FEATURE:
<221> NAME/KEY: MISC_FEATURE
<222> LOCATION: (101)..(101)
<223> OTHER INFORMATION: X is E, K, R, Y, I, or W
<220> FEATURE:
<221> NAME/KEY: MISC_FEATURE
<222> LOCATION: (117)..(117)
<223> OTHER INFORMATION: X is K, R, D, Y, or L
<220> FEATURE:
<221> NAME/KEY: MISC_FEATURE
<222> LOCATION: (119)..(119)
<223> OTHER INFORMATION: X is K, E, Y,  L, W, or I
<220> FEATURE:
<221> NAME/KEY: MISC_FEATURE
<222> LOCATION: (158)..(158)
<223> OTHER INFORMATION: X is Y, D, E, L, P, or I

<400> SEQUENCE: 46

Gly Val Phe Asn Tyr Glu Thr Glu Thr Thr Ser Val Ile Pro Ala Ala
1               5                   10                  15

Arg Leu Phe Lys Ala Phe Ile Leu Xaa Gly Asp Xaa Leu Phe Pro Lys
            20                  25                  30
```

```
Val Ala Pro Gln Ala Ile Ser Ser Val Glu Xaa Ile Glu Xaa Xaa Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Xaa
65                  70                  75                  80

Tyr Xaa Tyr Xaa Val Ile Glu Gly Gly Pro Ile Gly Asp Thr Leu Glu
                85                  90                  95

Lys Ile Xaa Asn Xaa Ile Lys Ile Val Ala Thr Pro Asp Gly Gly Ser
            100                 105                 110

Ile Leu Lys Ile Xaa Asn Xaa Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Xaa Asn
145                 150                 155
```

<210> SEQ ID NO 47
<211> LENGTH: 159
<212> TYPE: PRT
<213> ORGANISM: Betula verrucosa
<220> FEATURE:
<221> NAME/KEY: MISC_FEATURE
<222> LOCATION: (25)..(25)
<223> OTHER INFORMATION: X is D, K, R, Y, H, or L
<220> FEATURE:
<221> NAME/KEY: MISC_FEATURE
<222> LOCATION: (28)..(28)
<223> OTHER INFORMATION: X is N, K, R, Y, I, or W
<220> FEATURE:
<221> NAME/KEY: MISC_FEATURE
<222> LOCATION: (43)..(43)
<223> OTHER INFORMATION: X is N, Y, H, I, L, or E
<220> FEATURE:
<221> NAME/KEY: MISC_FEATURE
<222> LOCATION: (46)..(46)
<223> OTHER INFORMATION: X is G, P, V, D, T, or L
<220> FEATURE:
<221> NAME/KEY: MISC_FEATURE
<222> LOCATION: (47)..(47)
<223> OTHER INFORMATION: X is N, E, L, I, Y, or P
<220> FEATURE:
<221> NAME/KEY: MISC_FEATURE
<222> LOCATION: (80)..(80)
<223> OTHER INFORMATION: X is K, Y, E, W, I, or L
<220> FEATURE:
<221> NAME/KEY: MISC_FEATURE
<222> LOCATION: (82)..(82)
<223> OTHER INFORMATION: X is N, K, R, Y, E, or L
<220> FEATURE:
<221> NAME/KEY: MISC_FEATURE
<222> LOCATION: (84)..(84)
<223> OTHER INFORMATION: X is S, K, R, D, E, or Y
<220> FEATURE:
<221> NAME/KEY: MISC_FEATURE
<222> LOCATION: (99)..(99)
<223> OTHER INFORMATION: X is S, K, R, D, Y, or V
<220> FEATURE:
<221> NAME/KEY: MISC_FEATURE
<222> LOCATION: (101)..(101)
<223> OTHER INFORMATION: X is E, K, R, Y, I, or W
<220> FEATURE:
<221> NAME/KEY: MISC_FEATURE
<222> LOCATION: (117)..(117)
<223> OTHER INFORMATION: X is S, K, R, D, Y, or L
<220> FEATURE:
<221> NAME/KEY: MISC_FEATURE
<222> LOCATION: (119)..(119)
<223> OTHER INFORMATION: X is E, Y,  L, W, or I
<220> FEATURE:

-continued

```
<221> NAME/KEY: MISC_FEATURE
<222> LOCATION: (158)..(158)
<223> OTHER INFORMATION: X is Y, D, E, L, P, or I

<400> SEQUENCE: 47

Gly Val Phe Asn Tyr Glu Thr Glu Thr Thr Ser Val Ile Pro Ala Ala
1               5                   10                  15

Arg Leu Phe Lys Ala Phe Ile Leu Xaa Gly Asp Xaa Leu Phe Pro Lys
            20                  25                  30

Val Ala Pro Gln Ala Ile Ser Ser Val Glu Xaa Ile Glu Xaa Xaa Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Xaa
65                  70                  75                  80

Tyr Xaa Tyr Xaa Val Ile Glu Gly Gly Pro Ile Gly Asp Thr Leu Glu
                85                  90                  95

Lys Ile Xaa Asn Xaa Ile Lys Ile Val Ala Thr Pro Asp Gly Gly Ser
            100                 105                 110

Ile Leu Lys Ile Xaa Asn Xaa Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Xaa Asn
145                 150                 155
```